United States Patent
Toya

(10) Patent No.: US 10,512,426 B2
(45) Date of Patent: Dec. 24, 2019

(54) BIOLOGICAL INFORMATION ACQUISITION DEVICE AND BIOLOGICAL INFORMATION ACQUISITION METHOD

(71) Applicant: Seiko Epson Corporation, Tokyo (JP)

(72) Inventor: Takashi Toya, Chino (JP)

(73) Assignee: Seiko Epson Corporation (JP)

( * ) Notice: Subject to any disclaimer, the term of this patent is extended or adjusted under 35 U.S.C. 154(b) by 257 days.

(21) Appl. No.: 15/661,366

(22) Filed: Jul. 27, 2017

(65) Prior Publication Data
US 2018/0055428 A1 Mar. 1, 2018

(30) Foreign Application Priority Data
Aug. 24, 2016 (JP) ................................. 2016-163348

(51) Int. Cl.
| | |
|---|---|
| A61B 5/1455 | (2006.01) |
| A61B 5/00 | (2006.01) |
| G16H 40/63 | (2018.01) |
| G16H 50/30 | (2018.01) |
| A61B 5/145 | (2006.01) |

(52) U.S. Cl.
CPC ........ *A61B 5/14552* (2013.01); *A61B 5/0033* (2013.01); *A61B 5/0075* (2013.01); *A61B 5/1455* (2013.01); *A61B 5/14532* (2013.01); *A61B 5/489* (2013.01); *A61B 5/681* (2013.01); *G16H 40/63* (2018.01); *G16H 50/30* (2018.01); *A61B 5/0037* (2013.01); *A61B 2560/0475* (2013.01); *A61B 2562/0238* (2013.01); *A61B 2562/046* (2013.01)

(58) Field of Classification Search
CPC .............. A61B 5/14532; A61B 5/1455; A61B 5/14551; A61B 5/14552; A61B 2562/0238; A61B 2562/046
USPC ......................................... 600/476, 473, 478
See application file for complete search history.

(56) References Cited

U.S. PATENT DOCUMENTS 4,942,877 A * 7/1990 Sakai ................. A61B 5/14551
356/41
5,368,224 A * 11/1994 Richardson ........ A61B 5/02416
356/41

(Continued)

FOREIGN PATENT DOCUMENTS

| | | |
|---|---|---|
| JP | 2014-124455 A | 7/2014 |
| JP | 5617525 B2 | 11/2014 |

*Primary Examiner* — Etsub D Berhanu
*Assistant Examiner* — James Stewart Stambaugh, III
(74) *Attorney, Agent, or Firm* — Harness, Dickey & Pierce, P.L.C.

(57) ABSTRACT

A storage unit stores a cumulative light emitting frequency or a cumulative light emitting time of a light emitting element. In a case where the cumulative light emitting frequency is greater than a predetermined light emitting frequency or the cumulative light emitting time is longer than a predetermined light emitting time, a control unit causes the light emitting element to emit light toward a living body by increasing the light emitting frequency or the light emitting time at which the light emitting element emits the light in order to acquire a light receiving result once, compared to a setting light emitting frequency or a setting light emitting time. A light receiving unit acquires information of the living body, based on a light receiving result obtained by receiving the light which is emitted toward the living body and transmitted through the living body.

4 Claims, 17 Drawing Sheets

(56) References Cited

U.S. PATENT DOCUMENTS

| | | | | |
|---|---|---|---|---|
| 5,615,672 A | * | 4/1997 | Braig | A61B 5/14532 |
| | | | | 600/474 |
| 7,132,805 B2 | * | 11/2006 | Young | H05B 33/0818 |
| | | | | 315/308 |
| 7,652,239 B2 | * | 1/2010 | Ozaki | G09G 3/3208 |
| | | | | 250/208.1 |

* cited by examiner

BIOLOGICAL INFORMATION ACQUISITION DEVICE AND BIOLOGICAL INFORMATION ACQUISITION METHOD

BACKGROUND

1. Technical Field

The present invention relates to a biological information acquisition device and a biological information acquisition method using a biological information acquisition device.

2. Related Art

In the related art, a biological information acquisition device (blood component measurement device) is known which acquires biological information relating to a blood vessel or blood in the blood vessel (for example, refer to JP-A-2014-124455). JP-A-2014-124455 discloses the biological information acquisition device as follows. Light emitted from the light emitting element present at a light emitting position is acquired as a light receiving result by a light receiving element present at a light receiving position. The light receiving result is used so as to acquire the biological information.

However, according to the light emitting element in the biological information acquisition device disclosed in JP-A-2014-124455, a light quantity gradually decreases since currents are repeatedly applied. Therefore, the light emitting element which is frequently used has a problem in that the light quantity decreases and an S/N ratio decreases.

SUMMARY

An advantage of some aspects of the invention is to solve at least a part of the problems described above, and the invention can be implemented as the following forms or application examples.

Application Example 1

A biological information acquisition device according to this application example includes a light emitting unit that causes a plurality of light emitting elements to emit light so as to emit the light to a living body, a light receiving unit that receives the light transmitted through the living body, a control unit that controls the light emitting unit and the light receiving unit, and a storage unit that stores a program for controlling the control unit. The storage unit stores a cumulative light emitting frequency or a cumulative light emitting time of the light emitting element. In a case where the cumulative light emitting frequency is greater than a predetermined light emitting frequency or the cumulative light emitting time is longer than a predetermined light emitting time, the control unit causes the light emitting element to emit the light toward the living body by increasing the light emitting frequency or the light emitting time at which the light emitting element emits the light in order to acquire a light receiving result once, compared to a setting light emitting frequency or a setting light emitting time. The light receiving unit acquires information of the living body, based on a light receiving result obtained by receiving the light which is emitted toward the living body and transmitted through the living body.

According to this application example, the cumulative light emitting frequency or the cumulative light emitting time of the light emitting element to be repeatedly used is stored. In a case where the cumulative light emitting frequency is greater than the predetermined light emitting frequency or the cumulative light emitting time is longer than the predetermined light emitting time, the light emitting element is caused to emit the light by increasing the light emitting frequency or the light emitting time at which the light emitting element emits the light in order to acquire the light receiving result once, compared to the setting light emitting frequency or the setting light emitting time. In this manner, it is possible to secure a light quantity required for acquiring the light receiving result once, and it is possible to minimize a decrease in an S/N ratio of a light emitting result. Therefore, the information of the living body can be accurately acquired.

Application Example 2

In the biological information acquisition device according to the application example, it is preferable that the biological information acquisition device further includes a first light receiving unit that receives the light transmitted through a blood vessel portion serving as a measurement target of the living body, and a second light receiving unit that receives the light transmitted through a non-blood vessel portion of the living body.

According to this application example, the biological information acquisition device further includes the first light receiving unit that receives the light transmitted through the blood vessel portion serving as the measurement target of the living body, and the second light receiving unit that receives the light transmitted through the non-blood vessel portion of the living body. Therefore, the information of the living body in the blood vessel portion can be more accurately acquired by comparing two light receiving results with each other.

Application Example 3

In the biological information acquisition device according to the application example, it is preferable that the information of the living body is glucose concentration or oxygen saturation in the blood.

According to this application example, as the information of the living body, the glucose concentration or the oxygen saturation in the blood can be more accurately acquired.

Application Example 4

A biological information acquisition method according to this application example is a biological information acquisition method of acquiring biological information by using a biological information acquisition device including a light emitting unit that causes a plurality of light emitting elements to emit light so as to emit the light to a living body, a light receiving unit that receives the light transmitted through the living body, a control unit that controls the light emitting unit and the light receiving unit, and a storage unit that stores a program for controlling the control unit. The biological information acquisition method includes storing a cumulative light emitting frequency or a cumulative light emitting time of the light emitting element, causing the light emitting element to emit the light toward the living body by increasing the light emitting frequency or the light emitting time at which the light emitting element emits the light in order to acquire a light receiving result once, compared to a setting light emitting frequency or a setting light emitting time, in a case where the cumulative light emitting frequency is greater than a predetermined light emitting frequency or the cumulative light emitting time is longer than a predetermined light emitting time, and causing the light receiving unit to acquire information of the living body, based on a light receiving result obtained by receiving the light which is emitted toward the living body and transmitted through the living body.

According to this application example, the cumulative light emitting frequency or the cumulative light emitting time of the light emitting element to be repeatedly used is stored. In a case where the cumulative light emitting frequency is greater than the predetermined light emitting frequency or the cumulative light emitting time is longer than the predetermined light emitting time, the light emitting element is caused to emit the light by increasing the light emitting frequency or the light emitting time at which the light emitting element emits the light in order to acquire the light receiving result once, compared to the setting light emitting frequency or the setting light emitting time. In this manner, it is possible to secure the light quantity required for acquiring the light receiving result once, and it is possible to minimize the decrease in the S/N ratio of the light emitting result. Therefore, the information of the living body can be accurately acquired.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described with reference to the drawings. In the following respective drawings, a scale of each layer or each member is made different from an actual scale in order to provide each layer or each member with a recognizable size to some extent.

Embodiment 1

A1. Device Configuration

First, a configuration of a biological information acquisition device 10 according to this embodiment will be described with reference to FIGS. 1 to 5.

Figure 1:
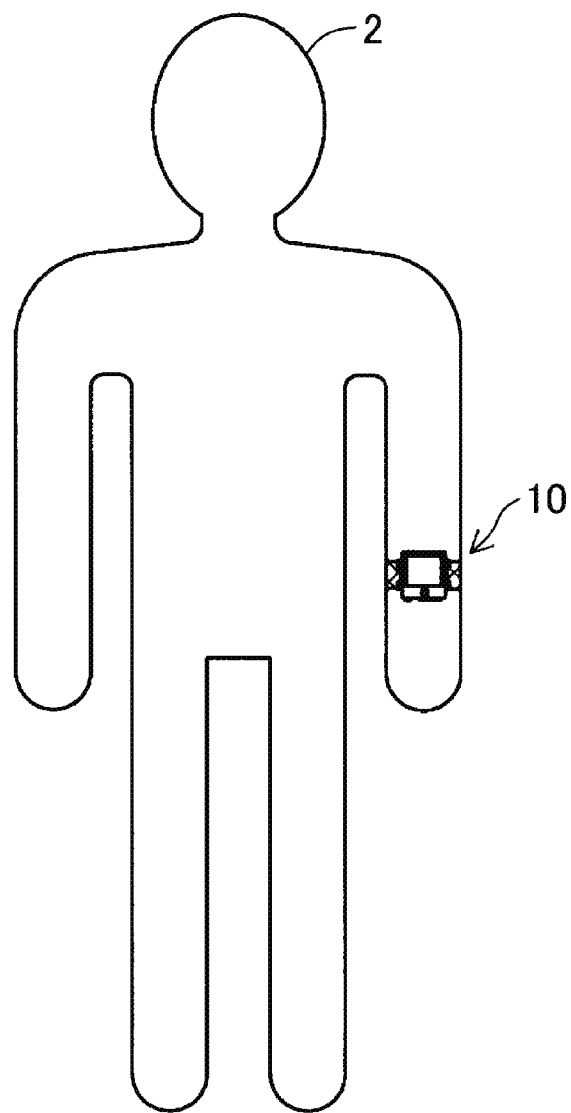
FIG. 1 is a schematic view illustrating a configuration of a biological information acquisition device according to Embodiment 1.
Figure 2:
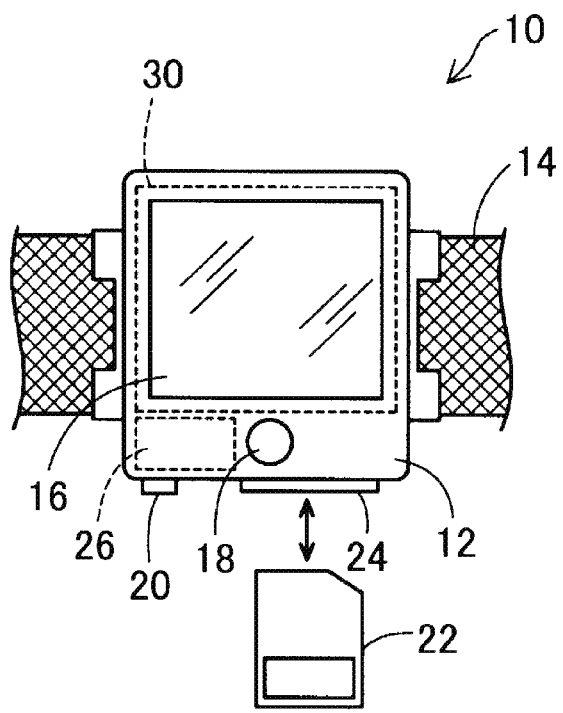
FIG. 2 is a schematic view illustrating a configuration of a front surface of the biological information acquisition device.
Figure 3:
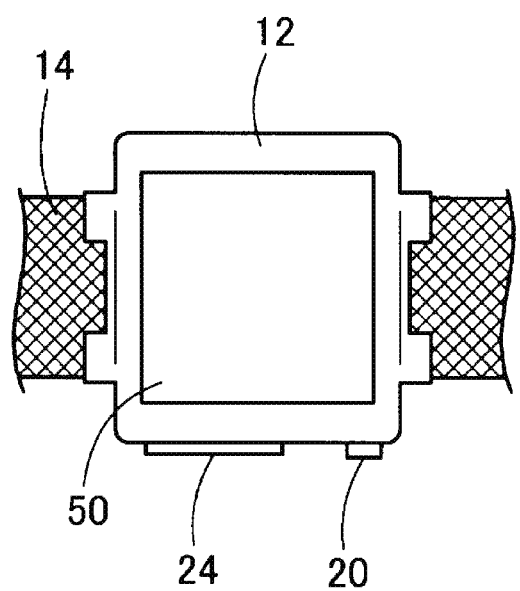
FIG. 3 is a schematic view illustrating a configuration of a rear surface of the biological information acquisition device.
Figure 4:
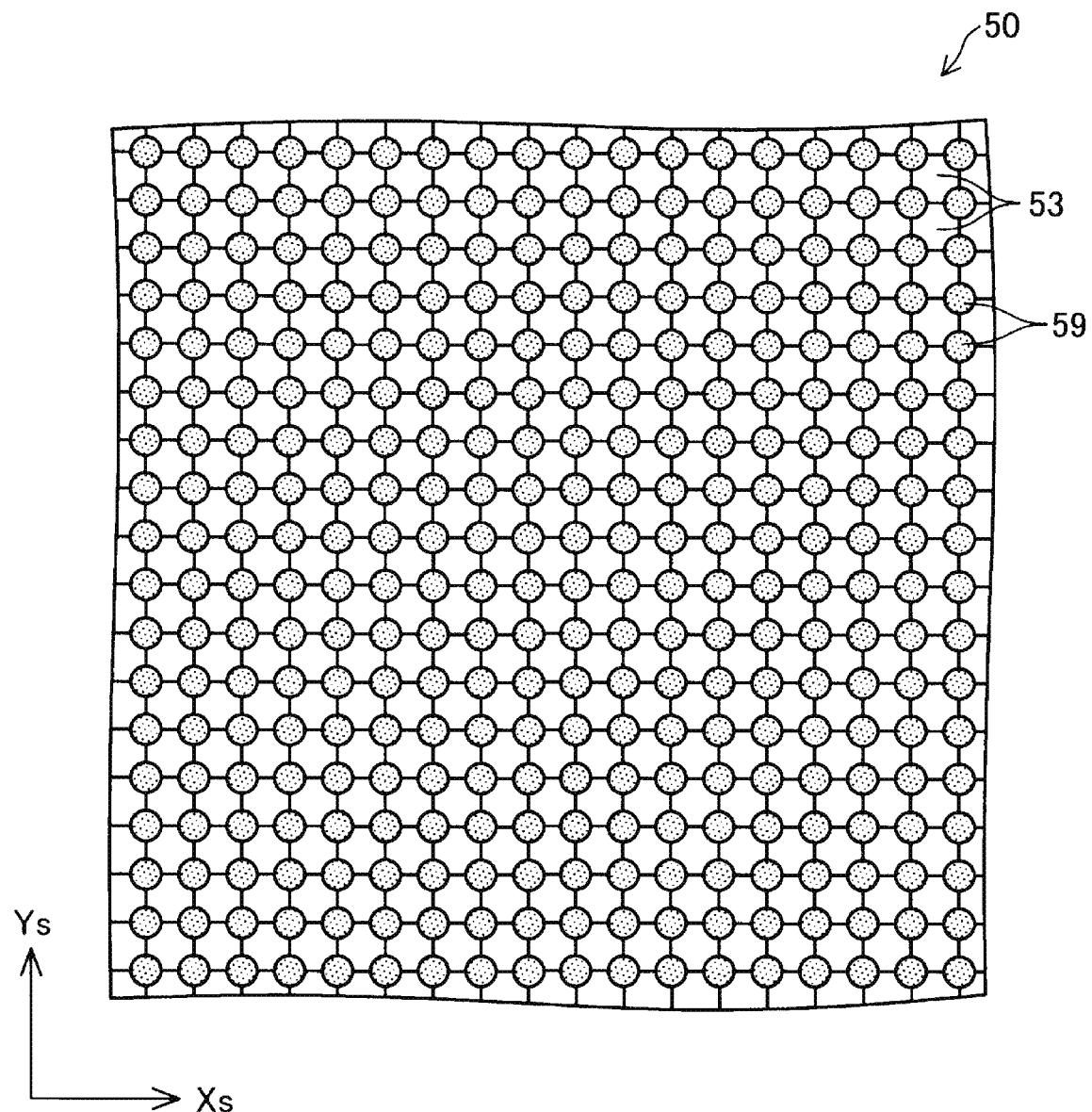
FIG. 4 is a schematic plan view illustrating a portion of a sensor module.
Figure 5:
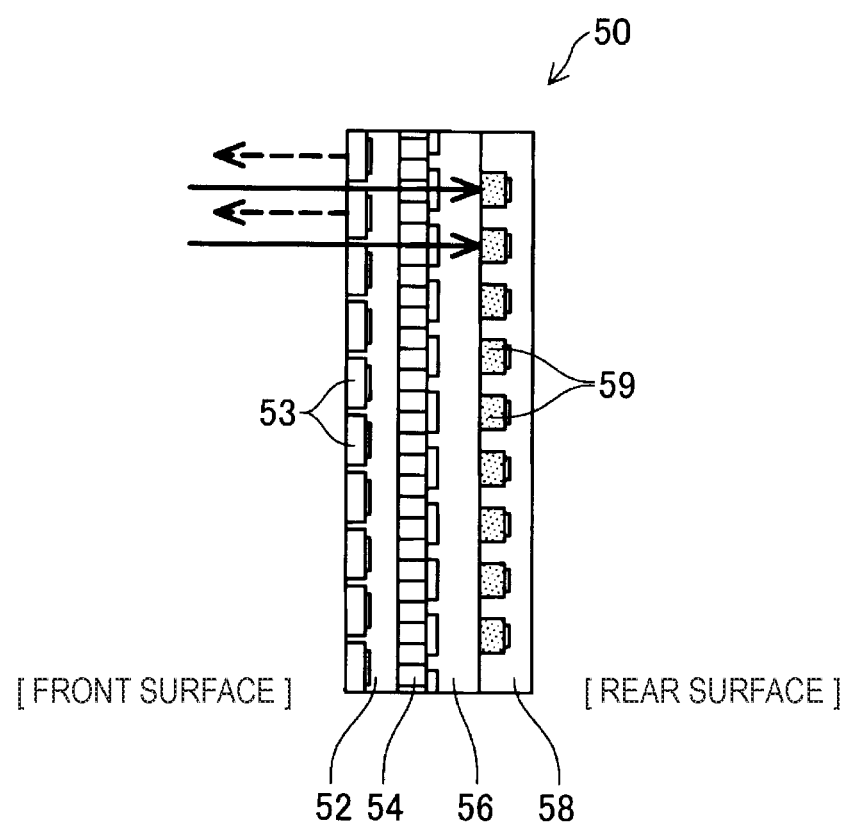
FIG. 5 is a schematic sectional view of the sensor module.

FIG. 1 is a schematic view illustrating the configuration of the biological information acquisition device 10 according to Embodiment 1. FIG. 2 is a schematic view illustrating a configuration of a front surface of the biological information acquisition device 10. FIG. 3 is a schematic view illustrating a configuration of a rear surface of the biological information acquisition device 10. FIG. 4 is a schematic plan view illustrating a portion of a sensor module 50. FIG. 5 is a schematic sectional view of the sensor module 50.

The biological information acquisition device 10 uses light so as to measure biological information of a user 2 in a non-invasive manner. In this embodiment, as an example, the biological information acquisition device 10 will be described in which a blood glucose level indicating glucose concentration in blood of the user 2 is acquired as the biological information. The biological information acquisition device 10 employs a wristwatch type, and is a wearable device (wearable instrument) configured to include a main body case 12 and a fixing band 14 for attaching and fixing the main body case 12 to a measurement target site such as a wrist and an arm of the user 2.

A touch panel 16 or an operation switch 18 is disposed on a front surface of the main body case 12 (surface facing outward when attached to the user 2). The touch panel 16 or the operation switch 18 is used so that the user 2 can input a measurement start instruction thereto or a measurement result can be displayed on the touch panel 16.

A communication device 20 for communicating with an external device and a reader/writer 24 of a memory card 22 are disposed on a side surface of the main body case 12. The communication device 20 is realized by a jack for attaching and detaching a wired cable, or by a wireless communication module and an antenna for wireless communication. The memory card 22 is a data rewritable nonvolatile memory such as a flash memory, a ferroelectric random access memory (FeRAM), and a magnetoresistive random access memory (MRAM).

The sensor module 50 is disposed on a rear surface of the main body case 12 so that the sensor module 50 can be in contact with a skin surface of the user 2. The sensor module 50 is a measurement-purpose device which emits measurement light to the skin surface of the user 2 and receives light transmitted through or reflected on the body of the user 2, and is a thin type image sensor internally equipped with a light source.

Furthermore, the main body case 12 is internally equipped with a rechargeable battery 26 and a control board 30. As a method for charging the battery 26, a configuration may be adopted in which an electrical contact is disposed on the rear surface side of the main body case 12 and the battery 26 is set in a cradle connected to a domestic power source so as to be charged via the electrical contact by way of the cradle. Alternatively, wireless charging may be employed.

The control board 30 is provided with a central processing unit (CPU), a main memory, a memory for measurement data, a touch panel controller, and a sensor module controller. The main memory is a storage medium which can store a program and initial set data or which can store computed values of the CPU. The main memory is realized by a RAM, a read only memory (ROM), and a flash memory. A configuration may be adopted in which the program and the initial set data are stored in the memory card 22. The memory for measurement data is a storage medium for storing the measurement data, and is realized by a data rewritable nonvolatile memory such as a flash memory, a ferroelectric memory (FeRAM), and a magnetoresistive memory (MRAM). A configuration may be adopted in which the measurement data is stored in the memory card 22.

As illustrated in FIG. 4, the sensor module 50 has a plurality of light emitting elements 53 and a plurality of the light receiving elements 59 which are respectively and regularly arranged in a light receiving and emitting region. Here, the light receiving and emitting region means a region including the plurality of light emitting elements 53 and the light receiving elements 59.

As illustrated in FIG. 5, the sensor module 50 is an optical sensor configured so that a light emitting layer 52 in which the plurality of light emitting elements 53 are two-dimensionally arranged in a planar fashion, a light blocking layer 54 which selectively blocks the light other than the light directed toward a light receiving layer 58, a spectral layer 56 which selectively transmits near infrared rays, and the light receiving layer 58 in which the plurality of the light receiving elements 59 are two-dimensionally arranged in a planar fashion are stacked one on another. The sensor module 50 is disposed on the rear surface side of the main body case 12 so that the front surface side (surface on the light emitting layer 52 side) faces the skin surface of the user 2.

The light emitting element 53 emits the light to the living body. For example, the light emitting element 53 is realized by a light emitting diode (LED) or an organic light emitting diode (OLED). In this embodiment, in order to measure a blood glucose level (glucose concentration in the blood), the light emitting element 53 can emit the light including near infrared rays having subcutaneously transmittance capability.

The light receiving element 59 receives the light transmitted through or reflected on the living body, and outputs an electric signal corresponding to the received light quantity. For example, the light receiving element 59 is realized by a charge coupled device (CCD) image sensor or a complementary metal oxide semiconductor (CMOS) image sensor. One light receiving element 59 includes a plurality of elements for receiving each wavelength component necessary for calibration.

As illustrated in FIG. 4, the light emitting element 53 and the light receiving element 59 are arranged in a matrix on a plane defined by a common Xs-Ys orthogonal coordinate system. The light emitting element 53 and the light receiving element 59 respectively have the same arrangement interval in Xs and Ys axis directions. However, both of these are arranged so as to be alternate on an Xs-Ys plane. That is, both of these are arranged so that positions of the light emitting element 53 and the light receiving element 59 in the Xs and Ys axis directions are shifted from each other by a predetermined length.

The arrangement interval between the light emitting element 53 and the light receiving element 59 can be appropriately set. For example, it is preferable to set the arrangement interval to 1 µm to 500 µm. In view of a balance between manufacturing cost and measurement accuracy, the arrangement interval can be set to 50 µm to 200 µm, for example. The light emitting element 53 and the light receiving element 59 may be juxtaposed with each other without being limited to a configuration in which the light emitting element 53 and the light receiving element 59 are stacked on each other.

A2. Measurement Principle

Next, a measurement principle of the blood glucose level by using the biological information acquisition device 10 according to this embodiment will be described with reference to FIGS. 6 to 11.

(A) Measurement of Blood Glucose Level

In order to measure the blood glucose level, the biological information acquisition device 10 is fixed to the user 2 with the fixing band 14 so that the sensor module 50 is in close contact with the skin surface of the user 2. Since the sensor module 50 is in close contact with the skin surface, it is possible to restrain factors that lower the measurement accuracy, such as reflection of the measurement light on the skin surface and scattering near the skin surface. Then, the blood vessel in the biological tissue directly below the sensor module 50 is set as a measurement target, and the measurement light receives the light including the transmitted light transmitted through the blood vessel so as to obtain an absorption spectrum. In this manner, the blood glucose level is estimated and calculated.

(A-1) Acquisition of Vascular Pattern

Specifically, first, a vascular pattern (blood vessel position) viewed from the skin surface is acquired. The acquisition of the vascular pattern can be realized in the same way as vein pattern detection in the known vein authentication technology.

Figure 6:
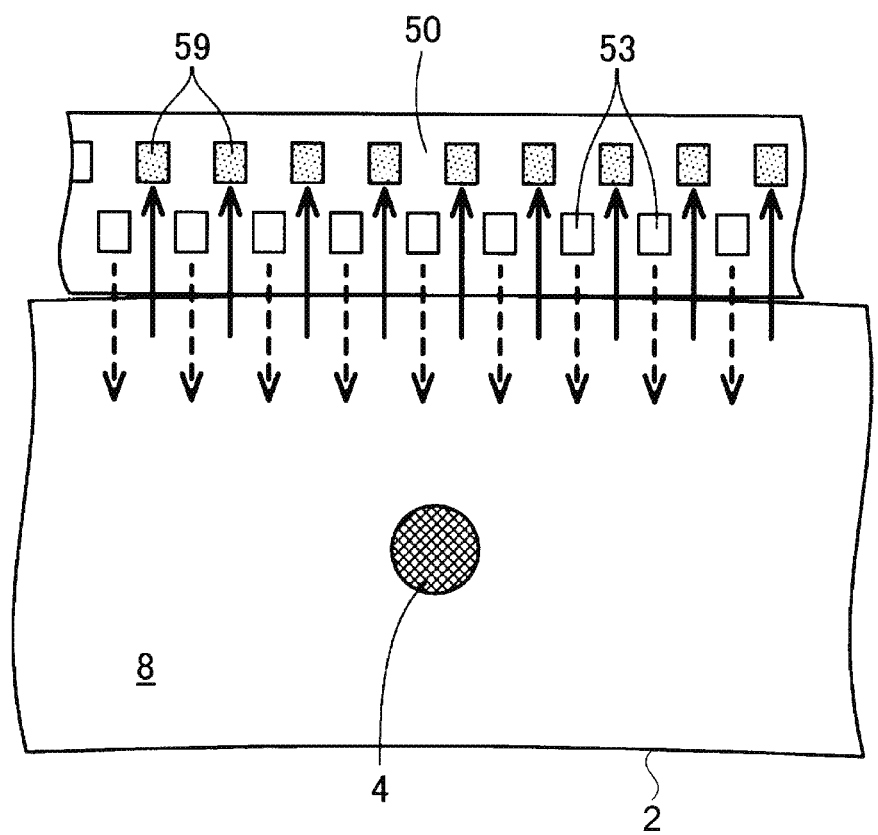
FIG. 6 is a schematic view for describing a state of acquiring a vascular pattern (blood vessel position).

FIG. 6 is a schematic view for describing a state of acquiring the vascular pattern (blood vessel position). As illustrated in FIG. 6, the light emitting elements 53 of the sensor module 50 are caused to emit the light all at once so as to emit the measurement light to the skin surface of the user 2. Then, the light receiving element 59 is used, and the measurement light receives (that is, images) the light transmitted through the biological tissue (transmitted light) or the light reflected on the biological tissue (reflected light), thereby acquiring a biological image. When the biological image is acquired, only some of the light emitting elements 53 of the sensor module 50 may be caused to emit the light.

The blood vessel 4 is more likely to absorb near infrared rays compared to a non-blood vessel portion (non-vascular region 8). Thus, in the acquired biological image, the blood vessel portion has lower luminance, and is darker than the non-blood vessel portion. Therefore, a portion having the lower luminance is extracted from the biological image. In this manner, the vascular pattern can be extracted. That is, it is determined whether or not the luminance of each pixel configuring the biological image is equal to or smaller than a predetermined threshold. In this manner, it is possible to determine whether or not the blood vessel exists directly below the corresponding light receiving element 59, that is, it is possible to acquire a position of the blood vessel.

Figure 7:
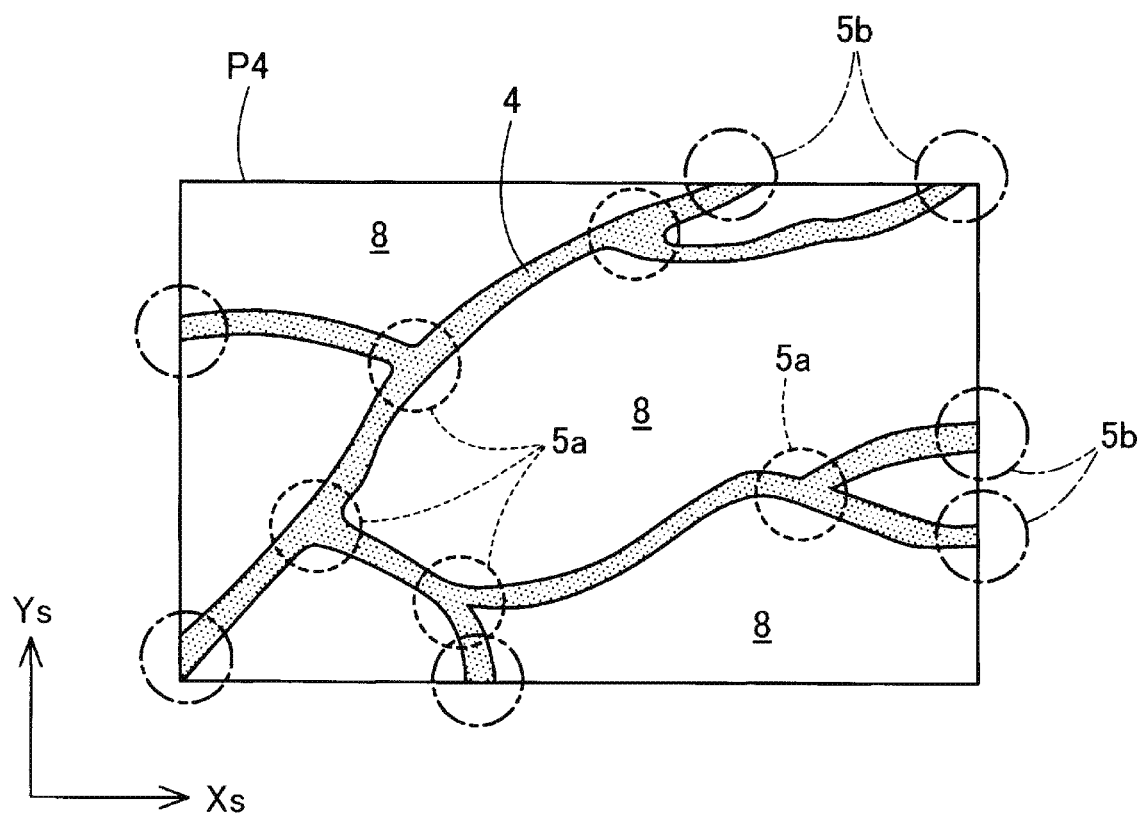
FIG. 7 illustrates an example of the vascular pattern obtained based on a biological image.

FIG. 7 illustrates an example of a vascular pattern P4 obtained based on the biological image. The vascular pattern P4 is information indicating whether a portion is the blood vessel 4 or the non-vascular region 8 for each pixel configuring the biological image, that is, for each position of the light receiving elements 59. In FIG. 7, a hatched band-like portion is the blood vessel 4, and other white outlined portions are extracted as the non-vascular region 8.

(A-2) Selection of Vascular Site as Measurement Target

If the vascular pattern is acquired, the blood vessel 4 (more specifically, the vascular site) serving as a measurement target is subsequently selected. The vascular site serving as the measurement target is selected so as to satisfy the following selection condition. The selection condition is that "the vascular site is a bifurcated portion or joined portion of the blood vessel and a portion other than an image end portion, and that the vascular site has a predetermined length and a predetermined width in the longitudinal direction of the blood vessel".

There is a possibility that the light passing through the blood vessel 4 other than the measurement target may be mixed with the received light in a bifurcated/joined portion 5a (refer to FIG. 7) of the blood vessel 4. The light transmitted through the blood vessel 4 other than the vascular site serving as the measurement target affects an absorption spectrum of the vascular site serving as the measurement target, thereby causing a possibility that measurement accuracy may become poor. Therefore, the vascular site serving as the measurement target is selected from the blood vessel portion other than the bifurcated/joined portion 5a of the blood vessel 4.

In an image end portion 5b (refer to FIG. 7) of the living body, a bifurcated or joined structure of the blood vessel 4 in the vicinity of the outside of the image is unknown. Accordingly, there is a possibility that the measurement accuracy may become poor due to the same reason as described above. In order to avoid this possibility, the vascular site serving as the measurement target is selected from the portion of the blood vessel 4 other than the image end portion 5b.

The light emitted from the light emitting element 53 is diffused and reflected inside the biological tissue, and the light is partially received by the light receiving element 59. In other words, the light partially received by the light receiving element 59 becomes the light transmitted through the blood vessel 4 serving as the target. As a proportion of the transmitted light becomes higher, the transmitted light can become an absorption spectrum which more remarkably shows the characteristics of the components contained in the blood of the blood vessel 4 serving as the target. That is, the measurement accuracy is improved.

The blood vessel 4 which is relatively thinly imaged (short blood vessel in the width direction) is the blood vessel 4 which is inherently thin, or is the blood vessel 4 which is located at a relatively deep position. In this blood vessel 4, the light quantity of the transmitted light decreases, and the measurement accuracy may become poor. Therefore, the vascular site serving as the measurement target is selected from the portion of the blood vessel 4 (that is, a vascular site having a predetermined width) excluding the portion of the blood vessel 4 which is thinly imaged.

Figure 8:
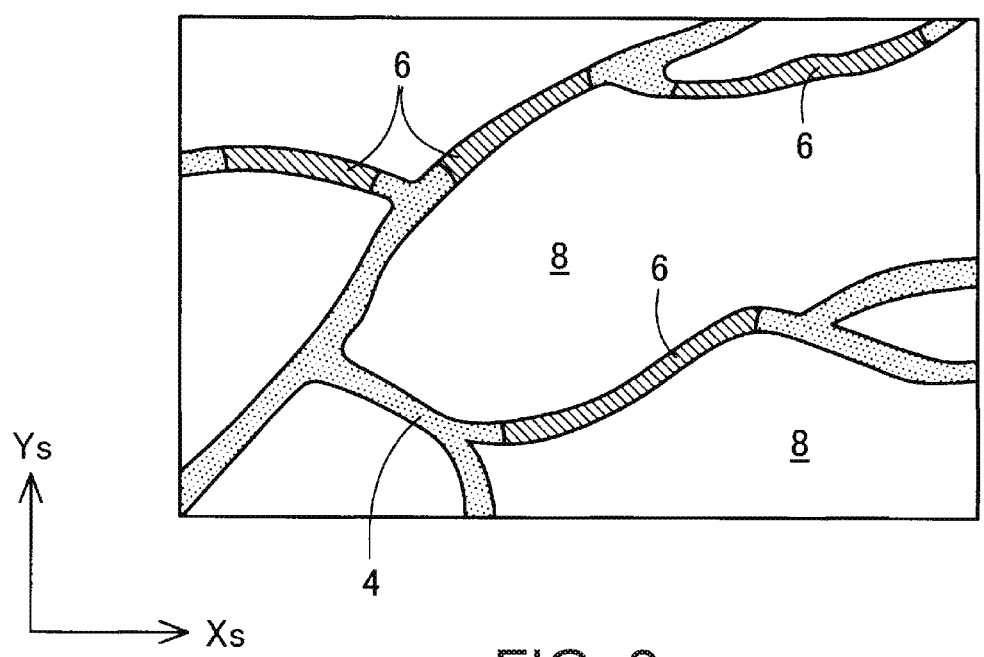
FIG. 8 illustrates an example of a vascular site serving as a measurement target obtained based on the vascular pattern illustrated in FIG. 7.

FIG. 8 is an example of a vascular site 6 serving as the measurement target obtained based on the vascular pattern P4 in FIG. 7. In FIG. 8, an obliquely hatched portion of the blood vessel 4 is the vascular site 6 selected as the measurement target.

(A-3) Selection of Light Emitting Unit and Light Receiving Unit

Subsequently, a light emitting unit L and a light receiving unit S are selected.

Figure 9:
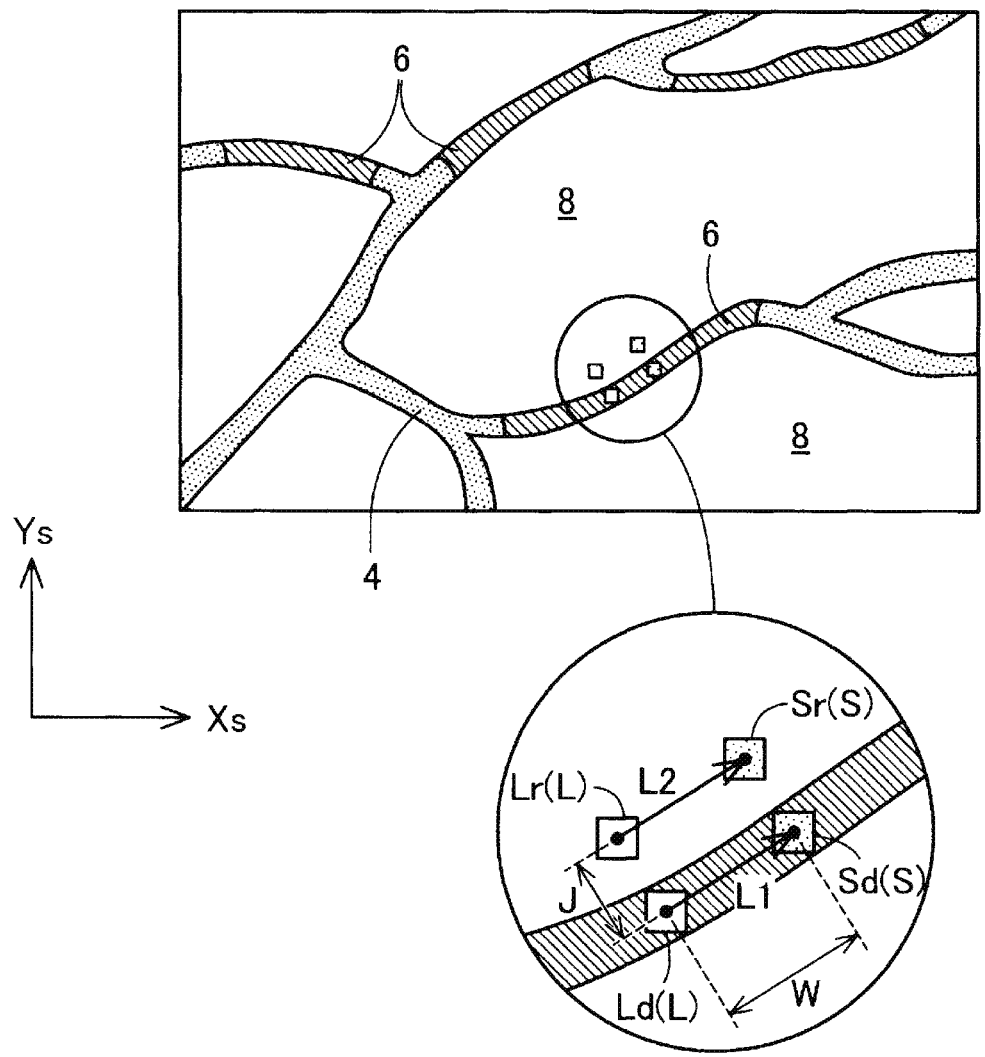
FIG. 9 is a view for describing selection between a light emitting unit and a light receiving unit.

FIG. 9 is a view for describing selection between the light emitting unit L and the light receiving unit S. In this embodiment, (i) the light emitting unit L located above the blood vessel 4 is selected as a measurement-purpose light emitting unit Ld, and (ii) the light receiving unit S separated from the measurement-purpose light emitting unit Ld by a predetermined distance W and located above the blood vessel 4 is selected as a first light receiving unit Sd serving as a measurement-purpose light receiving unit. Here, the term of "above the blood vessel" means that these are located above the vascular site 6 serving as the measurement target. Therefore, the measurement-purpose light receiving unit Sd receives the light transmitted through the blood vessel 4 serving as the blood vessel portion.

In addition, (iii) the light emitting unit L which is not located above the blood vessel 4 is selected as a reference-purpose light emitting unit Lr, and (iv) the light receiving unit S which is separated from the reference-purpose light emitting unit Lr by the predetermined distance W and is not located above the blood vessel 4 is selected as a second light receiving unit Sr serving as a reference-purpose light receiving unit. Here, the term of "not located above the blood vessel" means that these are not located above the blood vessel 4 including the vascular site 6 serving as the measurement target. Therefore, the reference-purpose light receiving unit Sr receives the light transmitted through the non-blood vessel portion (non-vascular region 8). The predetermined distance W is defined as follows.

Figure 10:
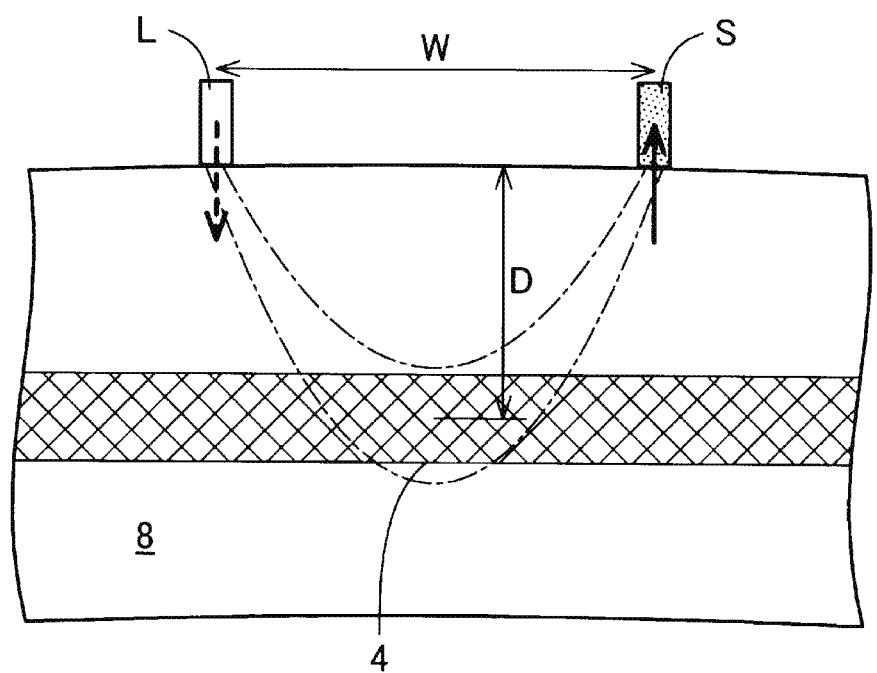
FIG. 10 is a view for describing light propagation inside a biological tissue.

FIG. 10 is a view for describing light propagation inside the biological tissue, and illustrates a sectional view taken along the depth direction. The light emitted from one of the light emitting units L is diffused and reflected inside the biological tissue, and the emitted light partially reaches the light receiving unit S. A propagation path of the light forms a so-called banana shape (region interposed between two arcs). The width in the depth direction is most widened in the vicinity of substantially the center, and the entire depth (reachable depth) is deepened in accordance with the interval between the light emitting element 53 and the light receiving element 59.

In order to improve the measurement accuracy, it is desirable that the more light transmitted through the blood vessel 4 is received by the light receiving unit S. From this viewpoint, it is preferable that the blood vessel 4 serving as the target is located below the light emitting unit L and the light receiving unit S. The predetermined distance W is determined in accordance with an assumed depth D of the blood vessel 4 serving as the target. The predetermined distance W, that is, the optimum interval W between the light emitting unit L and the light receiving unit S represents a distance approximately twice the distance D from the skin surface of the blood vessel 4. For example, if the depth D is approximately 3 mm, the optimum distance W is approximately 5 to 6 mm. Next, a relationship between the light emitting unit L and the light emitting element 53, and a relationship between the light receiving unit S and the light receiving element 59 will be described.

Figure 11:
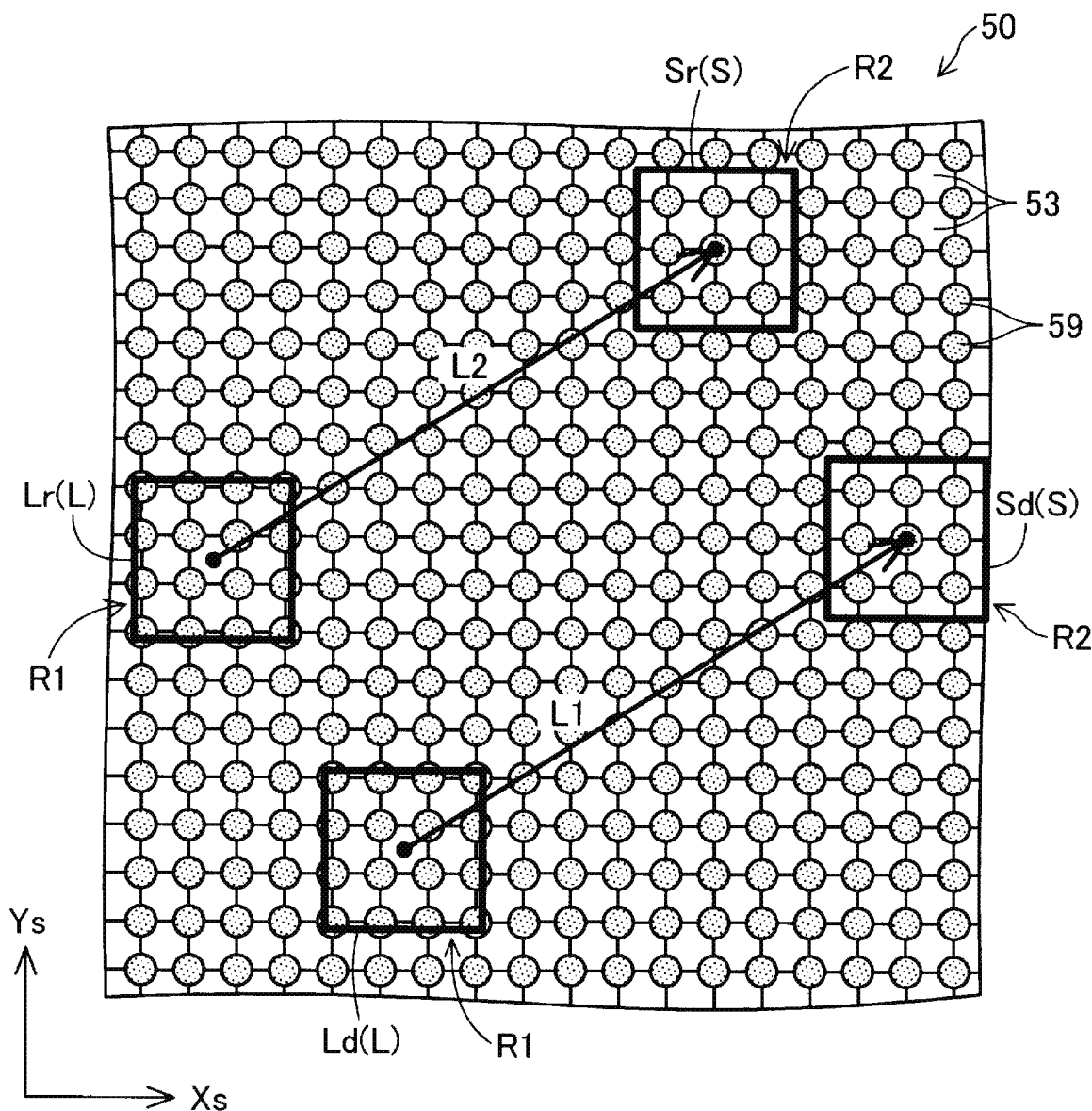
FIG. 11 illustrates a relationship between a light emitting unit and a light emitting element, and a relationship between the light receiving unit and the light receiving element.

FIG. 11 illustrates the relationship between the light emitting unit L and the light emitting element 53, and the relationship between the light receiving unit S and the light receiving element 59. The light emitting unit L in this embodiment is formed to include the plurality of light emitting elements 53 in a light emitting region R1. The light emitting region R1 is a partial region of the light receiving and emitting region of the sensor module 50, and means a region having a prescribed shape and size. In this embodiment, the light emitting region R1 is defined as a region in which three light emitting elements 53 are vertically (Ys-direction) located and three light emitting elements 53 are horizontally (Xs-direction) located. All of the light emitting elements 53 inside the light emitting region R1 are caused to emit the light as the light emitting unit L. In this embodiment, the sensor module 50 includes more than three of the light emitting elements 53 in the vertical direction (Ys-direction) and more than three of the light emitting elements 53 in the horizontal direction (Xs-direction). Therefore, the plurality of light emitting units L are present in the light receiving and emitting region of the sensor module 50. Then, a measurement-purpose light emitting unit Ld or a reference-purpose light emitting unit Lr is selected from the plurality of light emitting units L. A region including the plurality of light emitting elements 53 which are caused to emit the light as the measurement-purpose light emitting unit Ld is referred to as a first light emitting region, and a region including the plurality of light emitting elements 53 which are caused to emit the light as the reference-purpose light emitting unit Lr is referred to as a second light emitting region.

For example, the light emitting region R1 having the prescribed shape and size may be one region of the light emitting elements 53. In this case, one of the light emitting elements 53 inside this region serves as the light emitting unit L. It is not necessary to cause all of the light emitting elements 53 inside the light emitting region R1 to emit the light.

Similarly, the light receiving unit S in this embodiment is formed to include the plurality of light receiving elements 59 inside a light receiving region R2. The light receiving region R2 is a partial region of the light receiving and emitting region of the sensor module 50, and means a region having a prescribed shape and size. In this embodiment, the light receiving region R2 is defined as a region in which three light receiving elements 59 are vertically (Ys-direction) located and three light receiving elements 59 are horizontally (Xs-direction) located. All of the light receiving elements 59 inside the light receiving region R2 are caused to receive the light as the light receiving unit S. In this embodiment, the sensor module 50 includes more than three of the light receiving elements 59 in the vertical direction (Ys-direction) and more than three of the light receiving elements 59 in the horizontal direction (Xs-direction). Therefore, the plurality of light receiving units S are present in the light receiving and emitting region of the sensor module 50. Then, a measurement-purpose light receiving unit Sd or a reference-purpose light receiving unit Sr is selected from the plurality of light receiving units S. A region including the plurality of light receiving elements 59 which are caused to receive the light as the measurement-purpose light receiving unit Sd is referred to as a first light receiving region, and a region including the plurality of light receiving elements 59 which are caused to receive the light as the reference-purpose light receiving unit Sr is referred to as a second light receiving region.

For example, the light receiving region R2 having the prescribed shape and size may be one region of the light receiving elements 59. In this case, one of the light receiving elements 59 inside this light receiving region R2 serves as the light receiving unit S. It is not necessary to cause all of the light receiving elements 59 inside the light receiving region R2 to receive the light. In this embodiment, the predetermined distance W between the light emitting unit L and the light receiving unit S means a distance between a centroid of the light emitting region R1 and a centroid of the light receiving region R2. These centroids are geometric centroids determined depending on a shape of the region.

In this embodiment, a straight line L1 connecting the measurement-purpose light emitting unit Ld and the measurement-purpose light receiving unit Sd to each other and a straight line L2 connecting the reference-purpose light emitting unit Lr and the reference-purpose light receiving unit Sr are substantially parallel to each other. The term of "substantially parallel" means that an angle formed between the two straight lines L1 and L2 is within 10°. It is preferable that a distance J between the measurement-purpose light emitting unit Ld and the reference-purpose light emitting unit Lr is 6 mm or shorter. In this embodiment, the distance J is 5 mm.

(A-4) Measurement

If the measurement-purpose light emitting unit Ld, the measurement-purpose light receiving unit Sd, the reference-purpose light emitting unit Lr, and the reference-purpose light receiving unit Sr are selected for the vascular site 6 serving as the measurement target, the blood glucose level is measured. Specifically, first, the measurement-purpose light emitting unit Ld is caused to emit the light so as to acquire a light receiving result Q1 (referred to as a "first light receiving result Q1") of the light from the measurement-purpose light receiving unit Sd. Next, the reference-purpose light emitting unit Lr is caused to emit the light so as to acquire a light receiving result Q2 (referred to as a "second light receiving result Q2") of the light from the reference-purpose light receiving unit Sr. Then, an absorption spectrum is generated using the light receiving result Q1 and the light receiving result Q2.

In this case, for example, a wavelength of the emitted light is changed by the light emitting unit L. In this manner, a wavelength $\lambda$ of the light emitted to the skin surface is changed within the near infrared region, and transmittance T of the vascular site 6 is obtained for each wavelength $\lambda$. The transmittance $T(\lambda)$ is obtained as $T(\lambda)=Os(\lambda)/Or(\lambda)$, based on light intensity $Os(\lambda)$ obtained by the measurement-purpose light receiving unit Sd and light intensity $Or(\lambda)$ obtained by the reference-purpose light receiving unit Sr. Then, absorbance is obtained from the transmittance $T(\lambda)$ so as to generate the absorption spectrum.

Here, a calculation principle of the transmittance T will be briefly described. In general, if the intensity of the light emitted by the light emitting unit L is set to $P(\lambda)$, the transmittance of an object portion through which the emitted light is transmitted is set to $T(\lambda)$, and sensitivity determined in the light receiving unit S is set to $S(\lambda)$, the light intensity $O(\lambda)$ obtained by the light receiving unit S is expressed by $O(\lambda)=P(\lambda)\times T(\lambda)\times S(\lambda)$.

Based on this relational expression, the light intensity $Or(\lambda)$ obtained by the reference-purpose light receiving unit Sr which does not include the transmitted light of the blood vessel 4 is obtained as $Or(\lambda)=P(\lambda)\times S(\lambda)$, if the transmittance $T(\lambda)$ of the non-vascular region 8 is assumed as "1".

The light intensity $Os(\lambda)$ obtained by the measurement-purpose light receiving unit Sd which includes the transmitted light of the blood vessel 4 is expressed by $Os(\lambda)=P(\lambda)\times T(\lambda)\times S(\lambda)$. Based on these two expressions, the transmittance T(λ) is obtained. The transmittance T(λ) is a value relative to the transmittance T(λ) of the non-vascular region 8.

(A-5) Calculation of Blood Glucose Level

Subsequently, based on the absorption spectrum, the blood glucose level is estimated and calculated using a calibration curve showing a relationship between a predetermined blood glucose level (blood glucose concentration) and the absorbance. A technique itself for calculating the concentration of a predetermined component (glucose in this embodiment) from this absorption spectrum is known. In this embodiment, the known technique can be applied.

A3. Functional Configuration

Next, a functional configuration of the biological information acquisition device 10 according to this embodiment will be described with reference to FIGS. 12 to 15.

Figure 12:
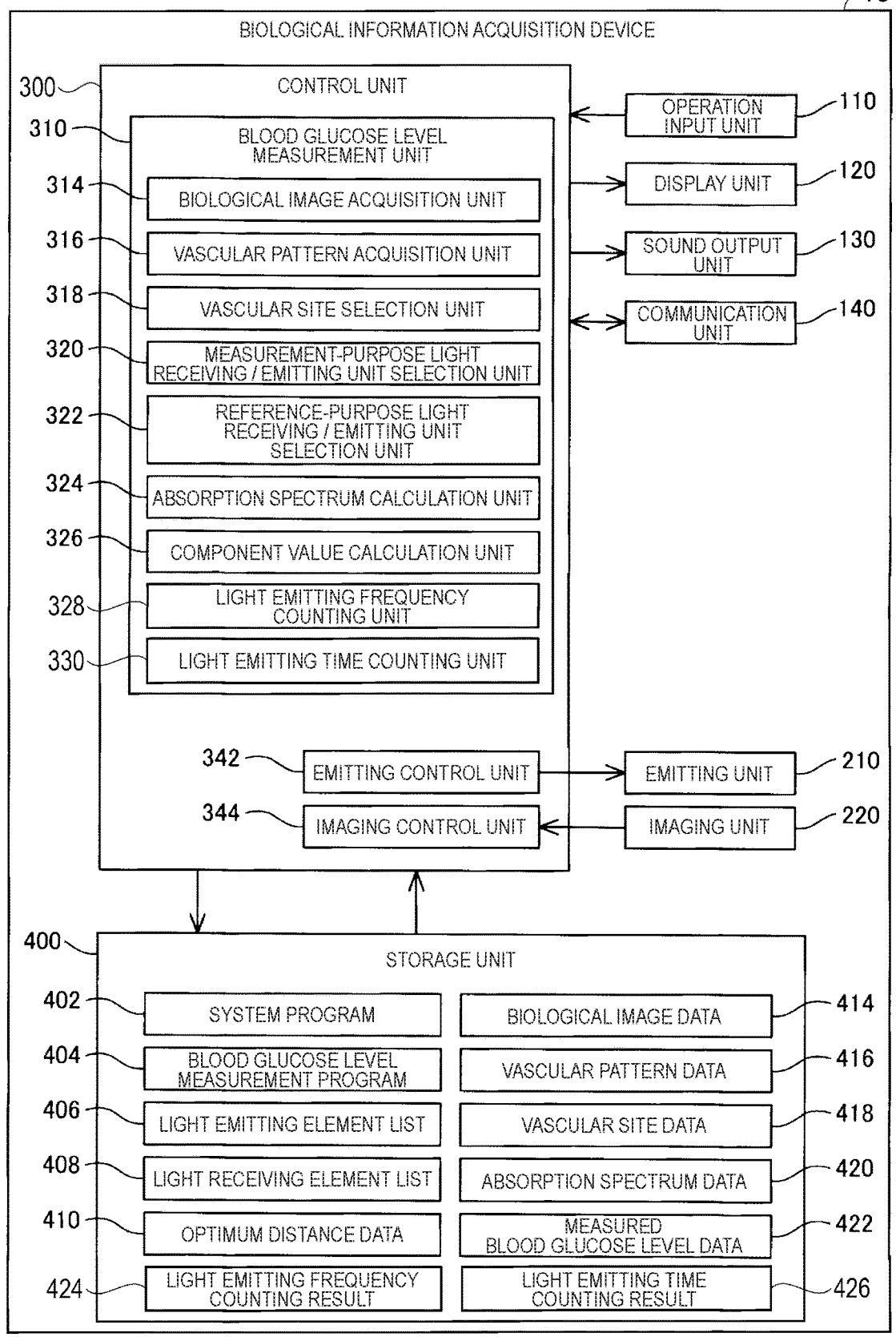
FIG. 12 is a functional configuration diagram of the biological information acquisition device according to Embodiment 1.
Figure 13:
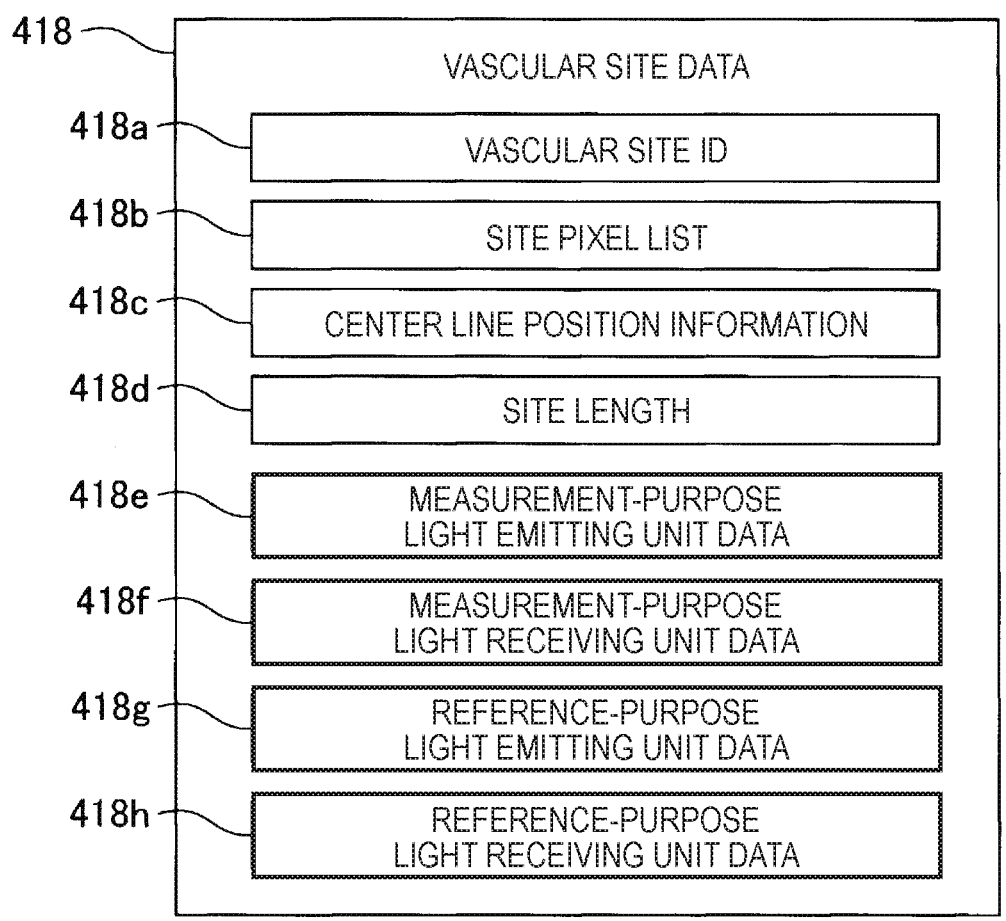
FIG. 13 illustrates an example of a data configuration of vascular site data.
Figure 14:
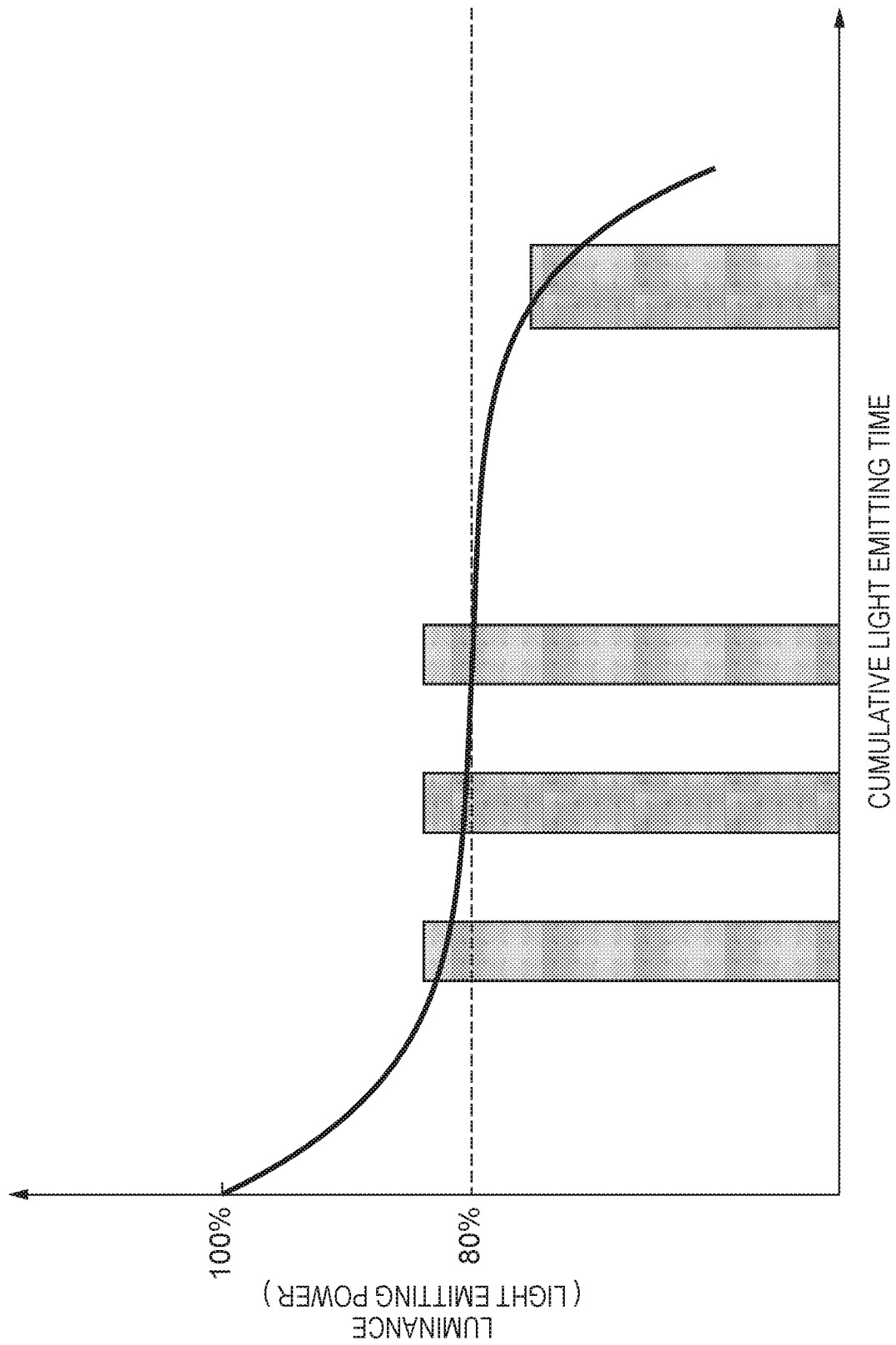
FIG. 14 illustrates a relationship between a cumulative light emitting time and luminance of the light emitting element.
Figure 15:
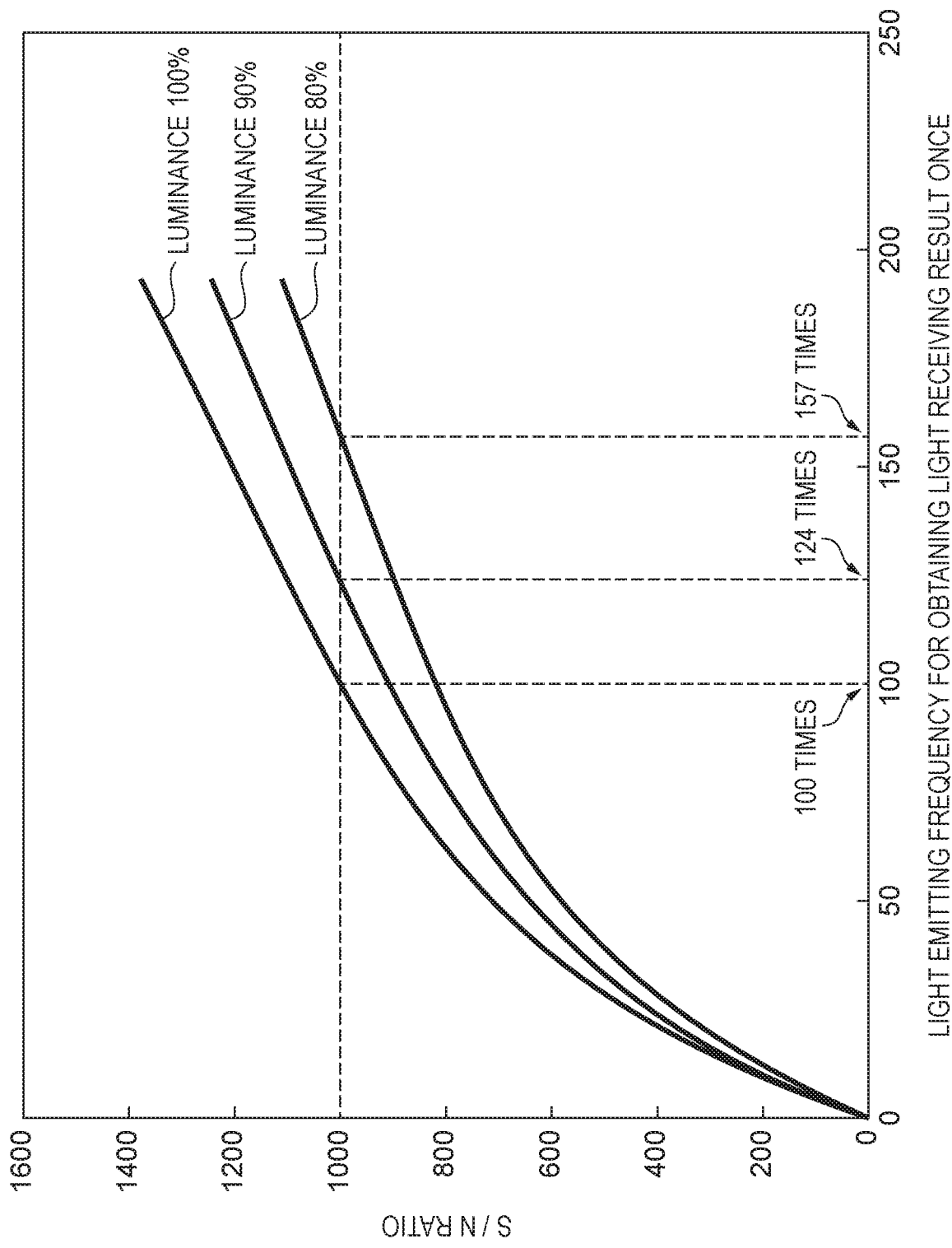
FIG. 15 illustrates a relationship between a light emitting frequency for obtaining a light receiving result once and an S/N ratio.

FIG. 12 is a functional configuration diagram of the biological information acquisition device 10 according to this embodiment. FIG. 13 illustrates an example of a data configuration of vascular site data 418. FIG. 14 illustrates a relationship between a cumulative light emitting time and luminance of the light emitting element 53. FIG. 15 illustrates a relationship between a light emitting frequency for obtaining a light receiving result once and an S/N ratio.

The biological information acquisition device 10 is configured to functionally include an operation input unit 110, a display unit 120, a sound output unit 130, a communication unit 140, a light emitting unit 210, an imaging unit 220, a control unit 300, and a storage unit 400.

The operation input unit 110 is an input device such as a button switch, a touch panel, and various sensors, and outputs an operation signal according to the operation to the control unit 300. The operation input unit 110 performs various instruction inputs such as instructions to start measurement of the blood glucose level. In FIG. 2, the operation switch 18 or the touch panel 16 corresponds to this operation input unit 110.

The display unit 120 is a display device such as a liquid crystal display (LCD), and performs various displays based on a display signal output from the control unit 300. The measurement result is displayed on the display unit 120. In FIG. 2, the touch panel 16 corresponds to this display unit 120.

The sound output unit 130 is a sound output device such as a speaker, and performs various sound outputs based on a sound signal output from the control unit 300. The sound output unit 130 outputs a notification sound for notifying the measurement start or the measurement completion of the blood glucose level, and generation of a low blood glucose level.

The communication unit 140 is a communication device such as a wireless communication device, a modem, a jack of a communication cable for wired communication, and a control circuit, and external communication is realized by being connected to a communication line. In FIGS. 2 and 3, the communication device 20 corresponds to this communication unit 140.

The light emitting unit 210 serving as the light emitting unit L has the plurality of light emitting elements 53 which are two-dimensionally arranged in a planar fashion. The light emitting layer 52 of the sensor module 50 illustrated in FIG. 5 corresponds to the light emitting unit 210. The arrangement position of the light emitting unit 210 (specifically, position coordinates of the respective light emitting elements 53 in the Xs-Ys orthogonal coordinate system) is stored as a light emitting element list 406 in the storage unit 400.

The imaging unit 220 serving as the light receiving unit S has the plurality of light receiving elements 59 which are two-dimensionally arranged in a planar fashion. The light receiving layer 58 of the sensor module 50 illustrated in FIG. 5 corresponds to the imaging unit 220. The arrangement position of the imaging unit 220 (specifically, position coordinates of the respective light receiving elements 59 in the Xs-Ys orthogonal coordinate system) is stored as a light receiving element list 408 in the storage unit 400.

For example, the control unit 300 is realized by microprocessors such as a CPU or a graphics processing unit (GPU) or electronic components such as an application specific integrated circuit (ASIC) and an IC memory. Based on predetermined programs and data or operation signals output from the operation input unit 110, the control unit 300 performs various arithmetic processes, and controls the operation of the biological information acquisition device 10. In FIG. 2, the control board 30 corresponds to this control unit 300. In addition, the control unit 300 has a blood glucose level measurement unit 310, a light emitting control unit 342, and an imaging control unit 344. The light emitting control unit 342 selectively controls the light emission of each of the plurality of light emitting elements 53. The imaging control unit 344 obtains the light quantity received from each of the plurality of the light receiving elements 59.

The blood glucose level measurement unit 310 has a biological image acquisition unit 314, a vascular pattern acquisition unit 316, a vascular site selection unit 318, a measurement-purpose light receiving/emitting unit selection unit 320, a reference-purpose light receiving/emitting unit selection unit 322, an absorption spectrum calculation unit 324, a component value calculation unit 326, a light emitting frequency counting unit 328, and a light emitting time counting unit 330. The blood glucose level measurement unit 310 measures the glucose concentration, that is, the blood glucose level in the blood of the user 2.

The biological image acquisition unit 314 acquires a biological image of the user 2. Acquisition of the biological image is realized by appropriately using a biological image capturing technique in the known vein authentication technology. That is, the light emitting elements 53 are caused to emit the light all at once, and the light receiving elements 59 measure (image) the light. Then, a luminance image based on the light measurement result, that is, the biological image is generated. The biological image acquired by the biological image acquisition unit 314 is stored as biological image data 414 in the storage unit 400.

The vascular pattern acquisition unit 316 performs predetermined image processing on the biological image acquired by the biological image acquisition unit 314 so as to acquire a vascular pattern. Specifically, the image processing is realized by appropriately using a technique for identifying a vein pattern from the biological image in the known vein authentication technology. For example, reference luminance is compared for each pixel of the biological image, and each pixel is subjected to binary coded processing and filter processing. The pixel whose luminance is lower than the reference luminance indicates the blood vessel 4, and the pixel whose luminance is equal to or higher than the reference luminance indicates the non-vascular region 8. The vascular pattern acquired by the vascular pattern acquisition unit 316 is stored as vascular pattern data 416 in the storage unit 400.

Based on the vascular pattern acquired by the vascular pattern acquisition unit 316, the vascular site selection unit 318 selects the vascular site 6 indicating a predetermined selection condition, as the measurement target. Here, the vascular site 6 serving as the measurement target may be one or more. Each of the vascular sites 6 selected as the measurement target is stored as the vascular site data 418 in the storage unit 400.

FIG. 13 illustrates an example of a data configuration of the vascular site data 418. The vascular site data 418 stores a vascular site ID 418*a* serving as identification information of the vascular site, a site pixel list 418*b*, center line position information 418*c*, a site length 418*d* which is a length in the longitudinal direction of the blood vessel, measurement-purpose light emitting unit data 418*e*, measurement-purpose light receiving unit data 418*f*, reference-purpose light emitting unit data 418*g*, and reference-purpose light receiving unit data 418*h*. The site pixel list 418*b* is a list of pixels (that is, the light receiving element 59) corresponding to the vascular site. The center line position information 418*c* is information on the position coordinates of the center line (center in the width direction of the blood vessel and a line along the longitudinal direction of the blood vessel) of the vascular site in the Xs-Ys orthogonal coordinate system.

The measurement-purpose light receiving/emitting unit selection unit 320 selects the measurement-purpose light emitting unit Ld and the measurement-purpose light receiving unit Sd for each of the vascular sites 6 serving as the measurement target. Specifically, one position on the center line of the vascular site 6 is selected as the measurement-purpose light emitting unit Ld in the Xs-Ys orthogonal coordinate system (that is, on the skin surface), and the measurement-purpose light receiving unit Sd which is separated from the measurement-purpose light emitting unit Ld by the predetermined distance W and which is located on the center line of the vascular site 6 is selected. A selection condition of the measurement-purpose light emitting unit Ld and the measurement-purpose light receiving unit Sd is referred to as a first condition. The predetermined distance W is stored as optimum distance data 410 in the storage unit 400. For example, a selection method of one position on the center line of the vascular site 6 is determined using substantially the center position in the longitudinal direction of the vascular site 6. The selected measurement-purpose light emitting unit Ld is stored as measurement-purpose light emitting unit data 418*e*, and the selected measurement-purpose light receiving unit Sd is stored as measurement-purpose light receiving unit data 418*f*.

In a case where the measurement-purpose light emitting unit Ld and the measurement-purpose light receiving unit Sd which satisfy the above-described first condition are not present, it is determined whether or not the measurement-purpose light emitting unit Ld and the measurement-purpose light receiving unit Sd which similarly satisfy the above-described first condition are present at a position separated from the one position by a predetermined unit distance along the center line of the vascular site 6. Nevertheless, in a case where the measurement-purpose light emitting unit Ld and the measurement-purpose light receiving unit Sd which satisfy the above-described first condition are not present, this process is similarly repeated. In this manner, the measurement-purpose light emitting unit Ld and the measurement-purpose light receiving unit Sd are searched for and selected.

Based on the measurement-purpose light emitting unit Ld and the measurement-purpose light receiving unit Sd which are set by the measurement-purpose light receiving/emitting unit selection unit 320, the reference-purpose light receiving/emitting unit selection unit 322 selects one position which is not located above the blood vessel 4, as the reference-purpose light emitting unit Lr, and selects the reference-purpose light receiving unit Sr which is separated from the reference-purpose light emitting unit Lr by the predetermined distance W and which is not located above the blood vessel 4. A selection condition of the reference-purpose light emitting unit Lr and the reference-purpose light receiving unit Sr is referred to as a second condition.

In this embodiment, as illustrated in FIG. 9, the reference-purpose light receiving unit Sr is selected in which the distance J between the measurement-purpose light emitting unit Ld and the reference-purpose light emitting unit Lr is 5 mm, and in which the straight line connecting the measurement-purpose light emitting unit Ld and the measurement-purpose light receiving unit Sd to each other and the straight line connecting the reference-purpose light emitting unit Lr and the reference-purpose light receiving unit Sr to each other are substantially parallel to each other. The above-described selection condition different from the first condition and the second condition is referred to as a third condition. In a case where the reference-purpose light emitting unit Lr and the reference-purpose light receiving unit Sr which satisfy the second condition and the third condition are not present, the measurement-purpose light receiving/emitting unit selection unit 320 searches for and selects the measurement-purpose light emitting unit Ld and the measurement-purpose light receiving unit Sd. The reference-purpose light emitting unit Lr is stored as reference-purpose light emitting unit data 418*g*, and the selected reference-purpose light receiving unit Sr is stored as reference-purpose light receiving unit data 418*h*.

The absorption spectrum calculation unit 324 generates an absorption spectrum for each of the vascular sites 6 serving as the measurement target. Specifically, based on the first light receiving result Q1 obtained from the measurement-purpose light receiving unit Sd and the second light receiving result Q2 obtained from the reference-purpose light receiving unit Sr, the transmittance T of each wavelength λ is calculated so as to generate the absorption spectrum. Furthermore, in a case where the plurality of vascular sites 6 serving as the measurement target are present, absorbance spectra of the plurality of respective vascular sites 6 serving as the measurement targets are averaged so as to calculate an average absorption spectrum. The absorption spectrum calculated by the absorption spectrum calculation unit 324 is stored as absorption spectrum data 420 in the storage unit 400.

Based on the absorption spectrum calculated by the absorption spectrum calculation unit 324, the component value calculation unit 326 calculates the glucose concentration (that is, the blood glucose level), which indicates the blood concentration of a target blood component. In this embodiment, the absorption spectrum is calculated using an analysis method such as a multiple regression analysis method, a principal component regression analysis method, a PLS regression analysis method, and an independent component analysis method. In a case where the plurality of vascular sites 6 serving as the measurement target are present, the blood glucose level is calculated from the average absorbance spectrum obtained by averaging the absorption spectra of the respective vascular sites 6. The blood glucose level calculated by the component value calculation unit 326 is accumulated and stored in the storage unit 400 as measured blood glucose level data 422 in association with the measurement time.

The light emitting time counting unit 330 counts a light emitting time for each light emitting element 53. That is, the light emitting time counting unit 330 counts the light emitting time of the light emitting elements 53 which emits the light during a setting light emitting time in order to acquire the light emitting result once in the measurement-purpose light emitting unit Ld selected by the measurement-purpose light receiving/emitting unit selection unit 320. Furthermore, the light emitting time counting unit 330 counts the light emitting time of the light emitting elements 53 which emits the light during a setting light emitting time in order to acquire the light emitting result once in the reference-purpose light emitting unit Lr selected by the reference-purpose light receiving/emitting unit selection unit 322. The total value of the light emitting time of the respective light emitting elements 53 is stored as a cumulative light emitting time in a light emitting time counting result 426 of the storage unit 400.

Here, the light emitting element 53 has a characteristic that the light quantity gradually decreases by repeatedly applying currents so as to emit the light. That is, in a case where a prescribed current value is continuously applied to the light emitting element 53, as illustrated in FIG. 14, as the cumulative light emitting time increases, the luminance (light emitting power) of the light emitting element 53 is gradually lowered, and falls below 80% serving as a threshold. Consequently, the light quantity necessary for obtaining the light receiving result once cannot be secured, thereby causing a problem in that an S/N ratio of the light emitting result decreases.

Therefore, if the light emitting time of the light emitting element 53 is assumed to be constant, as illustrated in FIG. 15, a light emitting frequency for obtaining the light receiving result once is increased as follows. The light emitting frequency is set to 100 times in a case of the luminance of 100%, the light emitting frequency is set to 124 times in a case of the luminance of 90%, and the light emitting frequency is set to 157 times in a case of the luminance of 80%. In this way, as the luminance of the light emitting element 53 is lowered, the light emitting frequency is increased. In this manner, it is possible to obtain a desired S/N ratio (for example, 1,000). The light quantity of the light emitting element 53 is proportional to the product of the light emitting frequency and the light emitting time. Accordingly, in a case where the light emitting frequency is constant, the light emitting time is lengthened as the luminance of the light emitting element 53 is lowered. In this manner, it is possible to obtain the desired S/N ratio (for example, 1,000).

Therefore, in FIG. 14, in a case where the cumulative light emitting time of the light emitting element 53 which emits the light at the setting light emitting frequency and the setting light emitting time which are set in order to obtain the light receiving result once exceeds a predetermined light emitting time below a luminance threshold (80%), the setting light emitting frequency is set to be constant, and the setting light emitting time is lengthened. In this manner, it is possible to obtain the S/N ratio required for obtaining the light receiving result once.

Therefore, in a case where the cumulative light emitting frequency of the respective light emitting elements 53 is greater than the predetermined light emitting frequency, the setting light emitting time set so far is increased and set again. That is, the setting light emitting time is set so as to be changed from 0.2 seconds to 0.3 seconds, for example. As a result of this setting change, even if the luminance (light emitting power) in the light emission once of the light emitting element 53 decreases as the light emitting time increases, it is possible to secure the light quantity required for acquiring the light receiving result once.

The light emitting frequency counting unit 328 counts the light emitting frequency for each of the light emitting elements 53. That is, the light emitting frequency counting unit 328 counts the light emitting frequency of the light emitting element 53 which emits the light at the setting light emitting frequency in order to acquire the light emitting result once in the measurement-purpose light emitting unit Ld selected by the measurement-purpose light receiving/emitting unit selection unit 320. Furthermore, the light emitting frequency counting unit 328 counts the light emitting frequency of the light emitting element 53 which emits the light at the setting light emitting frequency in order to acquire the light emitting result once in the reference-purpose light emitting units Lr selected by the reference-purpose light receiving/emitting unit selection unit 322. The total value of the light emitting frequencies of the respective light emitting elements 53 is stored as a cumulative light emitting frequency in a light emitting frequency counting result 424 of the storage unit 400.

Here, in a case where the cumulative light emitting frequency of the respective light emitting elements 53 is greater than the predetermined light emitting frequency, the setting light emitting frequency set so far is increased and set again. That is, the setting light emitting frequency is set so as to be changed from twice to 3 times, for example. As a result of this setting change, similarly to the above-described case where the light emitting time is increased and set, even if the luminance (light emitting power) in the light emission once of the light emitting element 53 decreases as the light emitting frequency increases, it is possible to secure the light quantity required for acquiring the light receiving result once.

In this embodiment, a case has been described where the light emitting frequency counting unit 328 and the light emitting time counting unit 330 which acquire the light emitting frequency and the light emitting time of the light emitting element 53 are mounted thereon at the same time. However, the invention is not limited thereto. Any one of these may be mounted thereon.

The storage unit 400 is a storage device such as a ROM, a RAM, and a hard disk, and stores programs and data for the control unit 300 to integrally control the biological information acquisition device 10. The storage unit 400 is used as a work region of the control unit 300, and temporarily stores calculation results obtained by the control unit 300 or operation data output from the operation input unit 110. In FIG. 2, the main memory or the measurement data memory mounted on the control board 30 corresponds to the storage unit 400. The storage unit 400 stores a system program 402, a blood glucose level measurement program 404, alight emitting element list 406, a light receiving element list 408, optimum distance data 410, biological image data 414, vascular pattern data 416, vascular site data 418, absorption spectrum data 420, measured blood glucose level data 422, a light emitting frequency counting result 424 including the setting light emitting frequency and the predetermined light emitting frequency, and a light emitting time counting result 426 including the setting light emitting time and the predetermined light emitting time.

A4. Biological Information Acquisition Method

Figure 17:
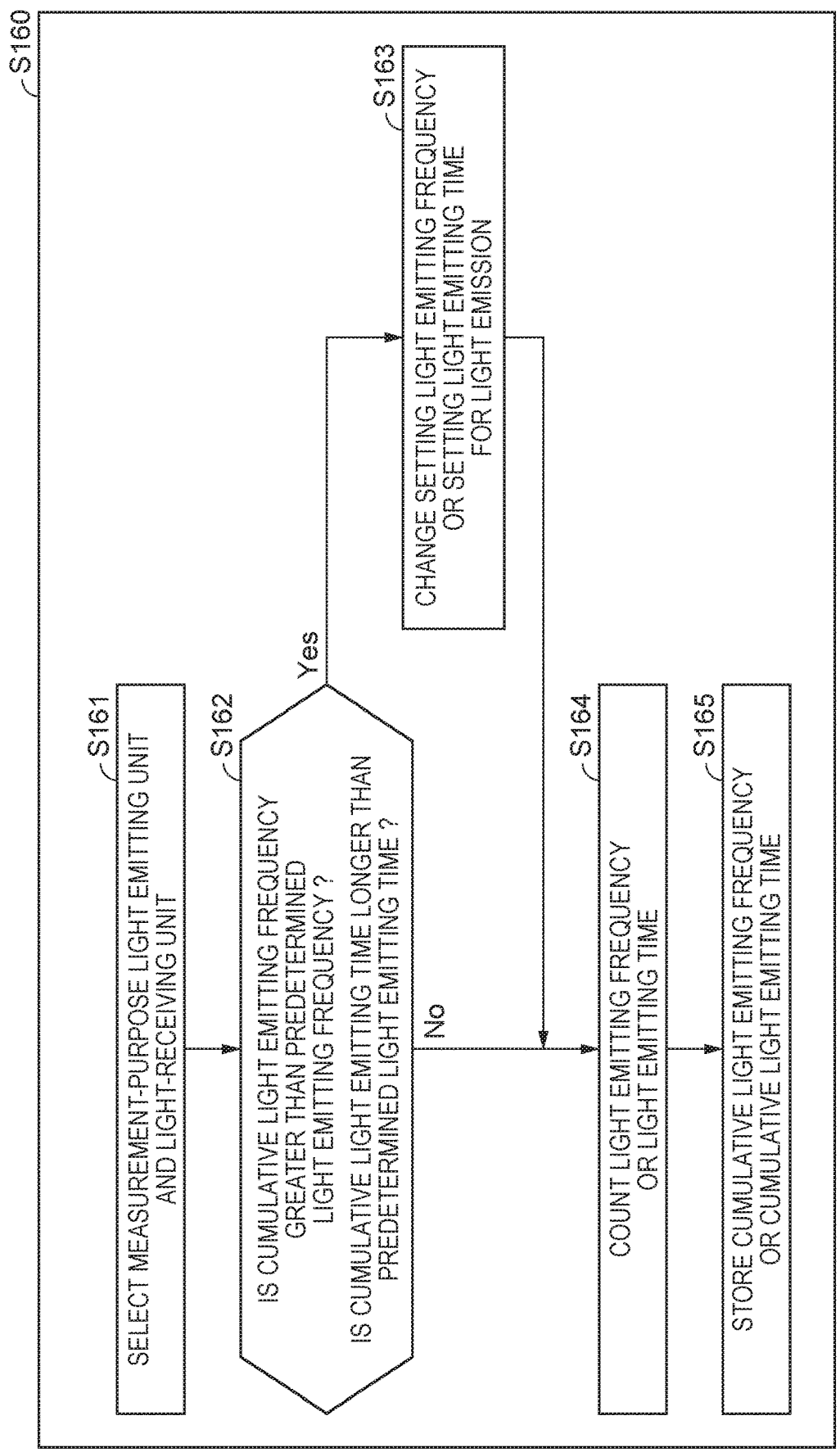
FIG. 17 is a view for specifically describing Step S160 in the blood glucose level measurement process.
Figure 18:
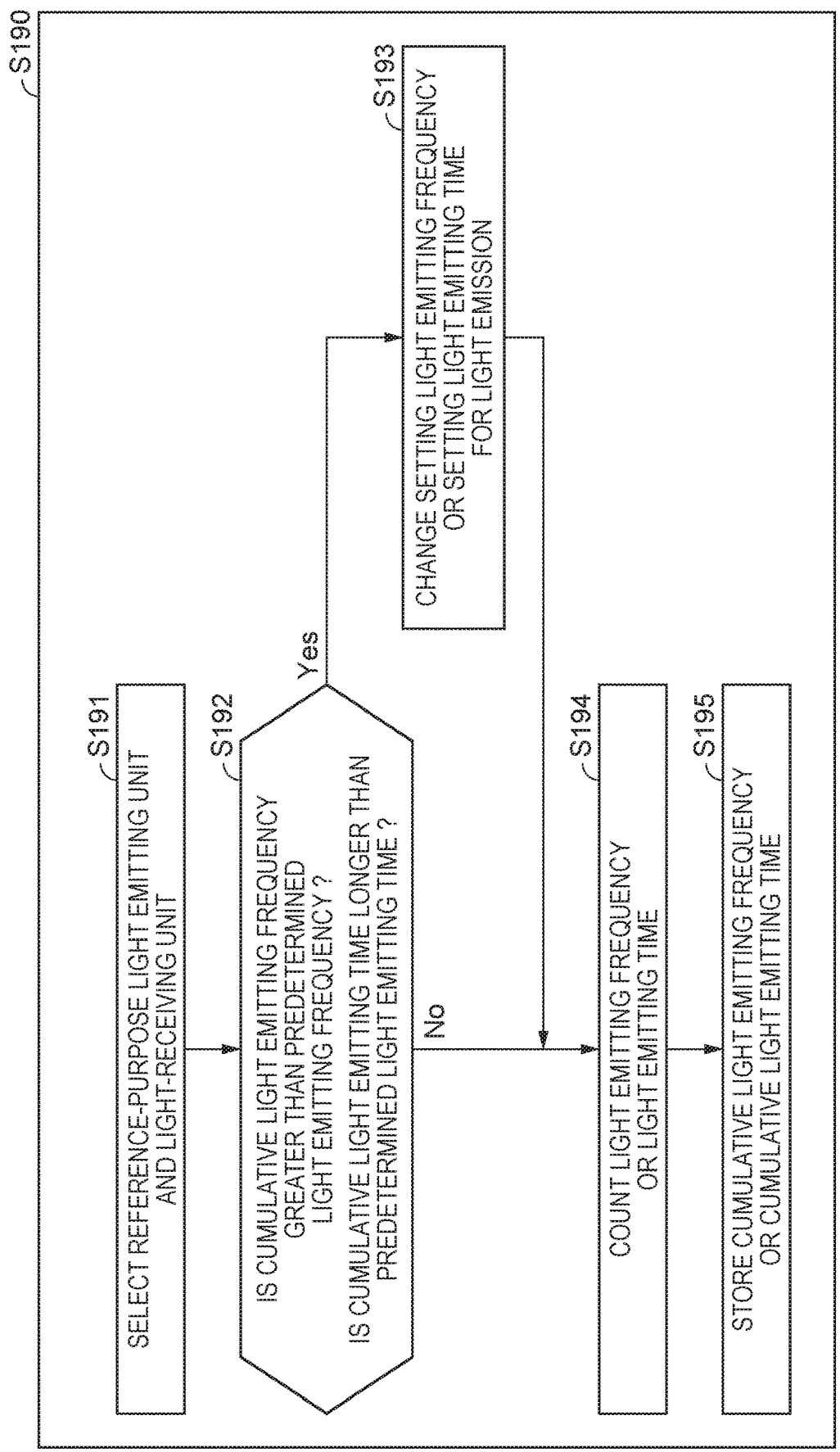
FIG. 18 is a view for specifically describing Step S190 in the blood glucose level measurement process.

Next, a biological information acquisition method according to this embodiment will be described with reference to FIGS. 16 to 18.

Figure 16:
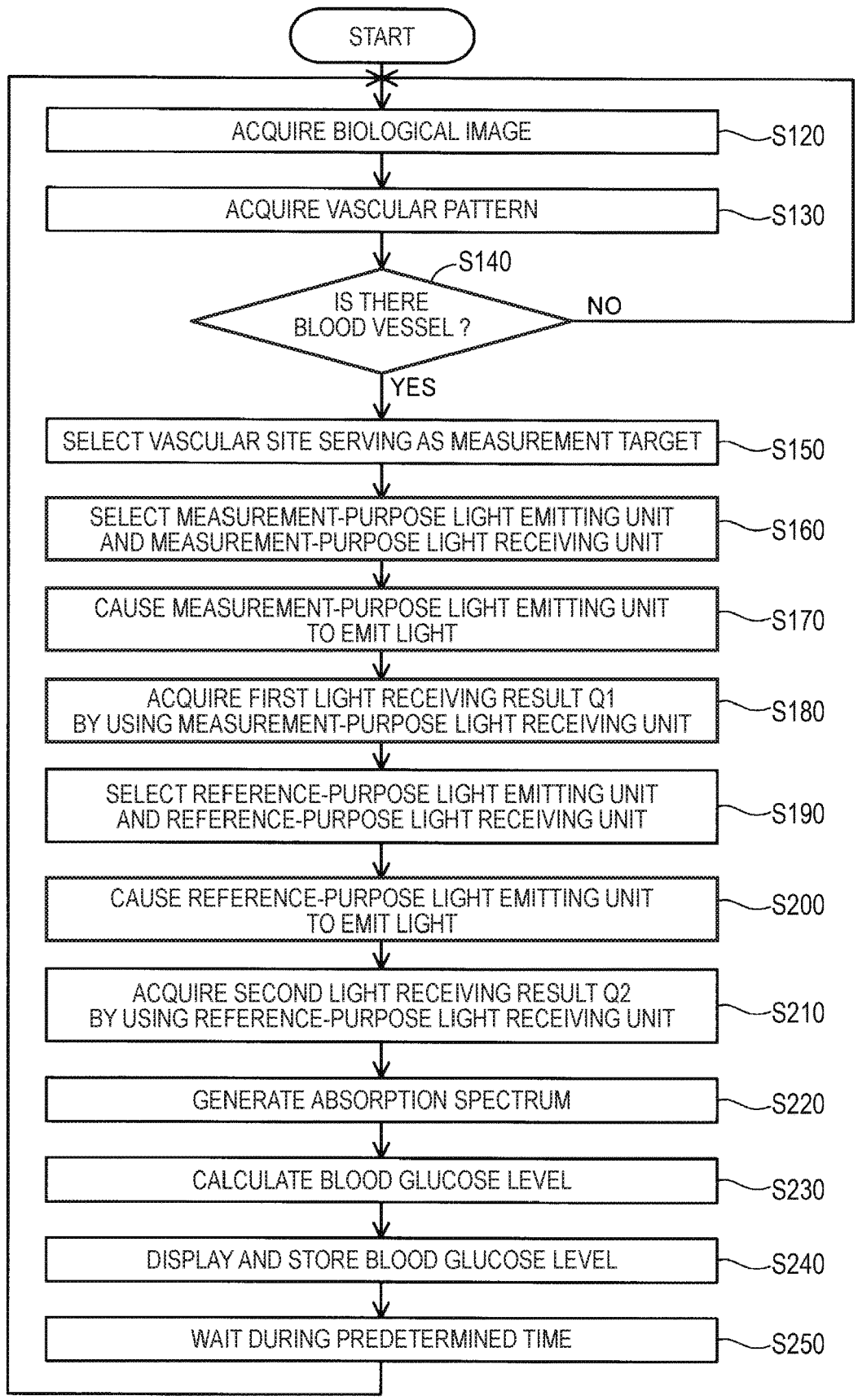
FIG. 16 is a flowchart for describing a flow of a blood glucose level measurement process.

FIG. 16 is a flowchart for describing a flow of a blood glucose level measurement process as the biological information acquisition method. FIGS. 17 and 18 are views for specifically describing Step S160 and Step S190 in the blood glucose level measurement process. The process is realized by the control unit 300 performing the process according to the blood glucose level measurement program 404.

As illustrated in FIG. 16, the blood glucose level measurement unit 310 performs a measurement process for measuring the blood glucose level of the user 2. First, the biological image acquisition unit 314 of the blood glucose level measurement unit 310 sets the entire surface of the light emitting surface of the sensor module 50 (that is, a range including all of the light emitting elements 53) as a light emitting range. The light emitting elements 53 within the light emitting range are caused to emit the light so as to obtain the biological image of the user 2 (Step S120). Subsequently, the vascular pattern acquisition unit 316 acquires the vascular pattern viewed from the skin surface, based on the obtained biological image (Step S130). As a result, if the vascular pattern cannot be obtained (Step S140: NO), the process returns to Step S120.

If the vascular pattern is obtained (Step S140: YES), the vascular site selection unit 318 selects the vascular site 6 serving as the measurement target which satisfies the predetermined selection condition, based on the obtained vascular pattern (Step S150). Next, based on the obtained vascular pattern, the measurement-purpose light receiving/emitting unit selection unit 320 selects the measurement-purpose light emitting unit Ld and the measurement-purpose light receiving unit Sd from the plurality of light emitting units L and light receiving units S (Step S160). In Step S160, as illustrated in FIG. 17, after the measurement-purpose light emitting unit Ld and the measurement-purpose light receiving unit Sd are selected (Step S161), it is determined whether the cumulative light emitting frequency of the light emitting elements 53 configuring the selected measurement-purpose light emitting unit Ld is greater than the predetermined light emitting frequency, or whether the cumulative light emitting time is longer than the predetermined light emitting time (Step S162).

In a case where the cumulative light emitting frequency of the light emitting elements 53 is equal to or smaller than the predetermined light emitting frequency, or in a case where the cumulative light emitting time is equal to or shorter than the predetermined light emitting time, the determination result in Step S162 is "No". The light emitting frequency or the light emitting time of the light emitting elements 53 is counted (Step S164). In Step S162, in a case where the cumulative light emitting frequency of the light emitting elements 53 is greater than the predetermined light emitting frequency, or in a case where the cumulative light emitting time is longer than the predetermined light emitting time, the determination result in Step S162 is "Yes". The setting light emitting frequency or the setting light emitting time set in order to acquire the light emitting result once is increased from the value set so far. In this manner, the setting light emitting frequency or the setting light emitting time is changed to the setting light emitting frequency or the setting light emitting time which can secure the light quantity necessary for obtaining the light receiving result once (Step S163).

Thereafter, the changed setting light emitting frequency or the changed setting light emitting time is added so as to count the light emitting frequency or the light emitting time of the light emitting elements 53 (Step S164). Next, the light emitting frequency or the light emitting time counted in Step S164 is stored as the cumulative light emitting frequency or the cumulative light emitting time in the light emitting frequency counting result 424 or the light emitting time counting result 426 of the storage unit 400 (Step S165).

Next, the measurement-purpose light emitting unit Ld is caused to emit the light at the setting light emitting frequency and the setting light emitting time which are set in order to obtain the light emitting result once (Step S170). The light emitted toward the living body by the measurement-purpose light emitting unit Ld and transmitted through the living body is received by the measurement-purpose light receiving unit Sd selected in Step S160 (Step S161), thereby obtaining the first Light receiving result Q1 (Step S180).

Thereafter, the reference-purpose light receiving/emitting unit selection unit 322 selects the reference-purpose light emitting unit Lr and the reference-purpose light receiving unit Sr from the plurality of light emitting units L and light receiving units S, based on the obtained vascular pattern (Step S190). In Step S190, as illustrated in FIG. 18, after the reference-purpose light emitting unit Lr and the reference-purpose light receiving unit Sr are selected (Step S191), it is determined whether the cumulative light emitting frequency of the light emitting elements 53 configuring the selected reference-purpose light emitting unit Lr is greater than the predetermined light emitting frequency, or whether the cumulative light emitting time is longer than the predetermined light emitting time (Step S192).

In a case where the cumulative light emitting frequency of the light emitting elements 53 is equal to or smaller than the predetermined light emitting frequency, or in a case where the cumulative light emitting time is equal to or shorter than the predetermined light emitting time, the determination result in Step S192 is "No". The light emitting frequency or the light emitting time of the light emitting elements 53 is counted (Step S194). In Step S192, in a case where the cumulative light emitting frequency of the light emitting elements 53 is greater than the predetermined light emitting frequency, or in a case where the cumulative light emitting time is longer than the predetermined light emitting time, the determination result in Step S192 is "Yes". The setting light emitting frequency or the setting light emitting time set in order to acquire the light emitting result once is increased from the value set so far. In this manner, the setting light emitting frequency or the setting light emitting time is changed to the setting light emitting frequency or the setting light emitting time which can secure the light quantity necessary for obtaining the light receiving result once (Step S193).

Thereafter, the changed setting light emitting frequency or the changed setting light emitting time is added so as to count the light emitting frequency or the light emitting time of the light emitting elements 53 (Step S194). Next, the light emitting frequency or the light emitting time counted in Step S194 is stored as the cumulative light emitting frequency or the cumulative light emitting time in the light emitting frequency counting result 424 or the light emitting time counting result 426 of the storage unit 400 (Step S195).

Next, the reference-purpose light emitting unit Lr is caused to emit the light at the setting light emitting frequency and the setting light emitting time set in order to acquire the light emitting result once (Step S200). The second light receiving result Q2 is obtained by the selected reference-purpose light receiving unit Sr (Step S210). A predetermined time interval is provided between the step of acquiring the first light receiving result Q1 (Step S180) and the step of acquiring the second light receiving result Q2 (Step S210). In the present embodiment, an interval of 5 seconds is provided as the predetermined time interval.

Next, the absorption spectrum calculation unit 324 generates the absorption spectrum for the vascular site 6 by using the first light receiving result Q1 and the second light receiving result Q2 (Step S220). Furthermore, in a case where the plurality of vascular sites 6 serving as the measurement target are present, the absorption spectrum obtained by averaging the absorption spectra of the respective vascular sites 6 is calculated.

Thereafter, as a step of acquiring the blood glucose level which indicates the information of the living body, based on the absorption spectrum, the component value calculation unit 326 uses the light receiving results Q1 and Q2 so as to calculate the glucose concentration in the blood, that is, the blood glucose level (Step S230). Next, the calculated blood glucose level is displayed on the display unit 120, and is cumulatively stored in association with the measurement time (Step S240). After a predetermined waiting time elapses (Step S250), the process returns to Step S120, and the subsequent blood glucose level is similarly measured.

As described above, according to the biological information acquisition device 10 and the biological information acquisition method in this embodiment, the following advantageous effects can be obtained.

The cumulative light emitting frequency or the cumulative light emitting time of the repeatedly used light emitting elements 53 is stored. In a case where the cumulative light emitting frequency is greater than the predetermined light emitting frequency, or in a case where the cumulative light emitting time is longer than the predetermined light emitting time, the light emitting element 53 is caused to emit the light by increasing the light emitting frequency or the light emitting time at which the light emitting element 53 emits the light in order to obtain the light receiving result once, compared to the setting light emitting frequency or the setting light emitting time. Therefore, it is possible to secure the light quantity required for acquiring the light receiving result once, and it is possible to minimize the decrease in the S/N ratio of the light emitting result. Accordingly, the blood glucose level which indicates the information of the living body can be accurately acquired.

The biological information acquisition device 10 includes the measurement-purpose light receiving unit serving as the first light receiving unit Sd which receives the light transmitted through the blood vessel portion (blood vessel 4) serving as the measurement target of the living body, and the reference-purpose light receiving unit serving as the second light receiving unit Sr which receives the light transmitted through the non-blood vessel portion (non-vascular region 8) of the living body. Therefore, the first light receiving result Q1 in the measurement-purpose light receiving unit Sd and the second light receiving result Q2 in the reference-purpose light receiving unit Sr are compared with each other. In this manner, the blood glucose level which indicates the information of the living body in the blood vessel portion (blood vessel 4) can be more accurately acquired.

Embodiment 2

Next, a biological information acquisition method according to Embodiment 2 will be described with reference to FIG. 19.

Figure 19:
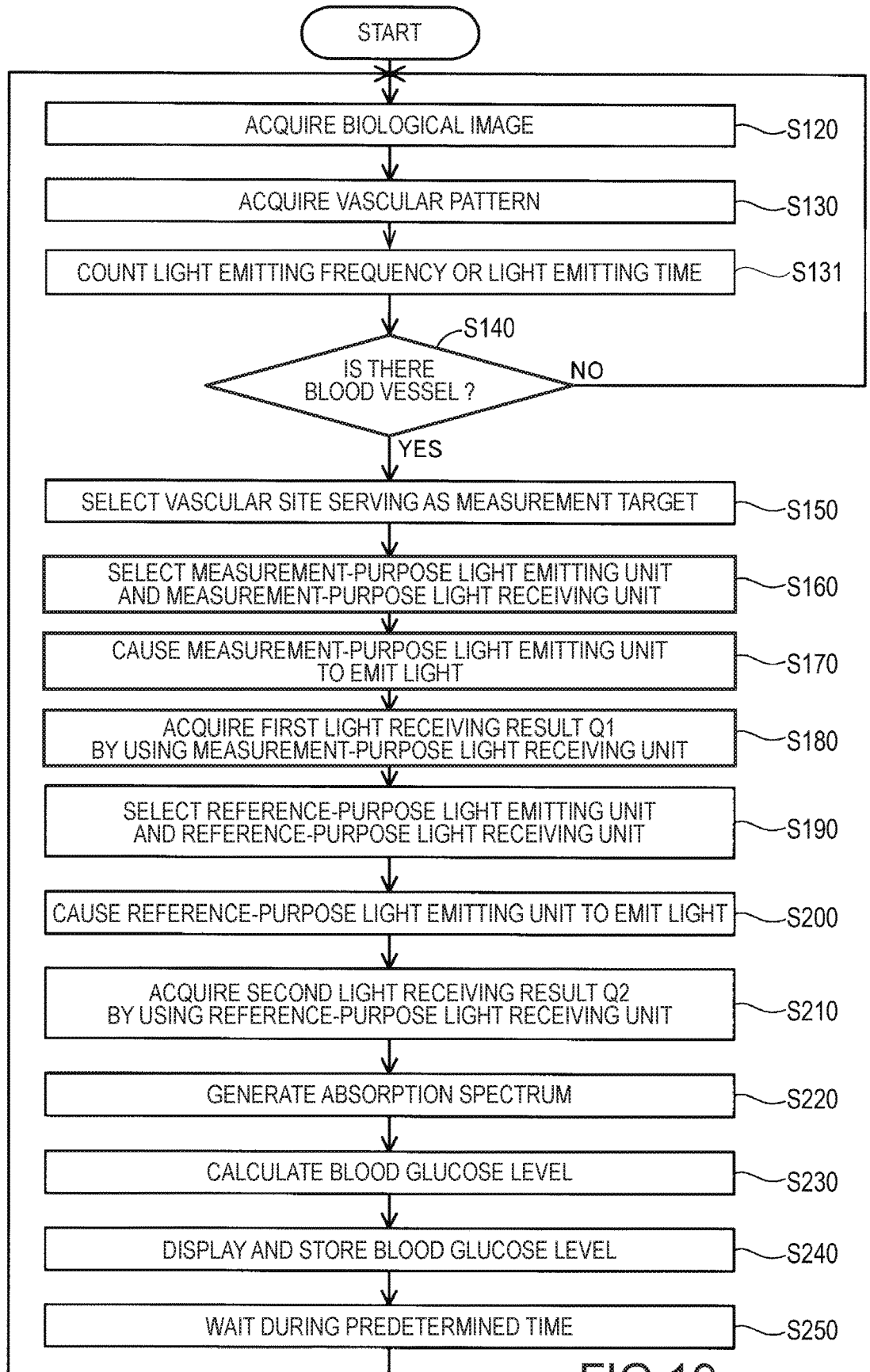
FIG. 19 is a flowchart for describing a flow of a blood glucose level measurement process according to Embodiment 2.

FIG. 19 is a flowchart for describing a flow of a blood glucose level measurement process according to Embodiment 2. The same numbers will be given to processes the same as those in Embodiment 1, and repeated description will be omitted.

In Embodiment 2, the light emitting frequency or the light emitting time is also counted for the light emitting elements 53 which emit the light when the biological image is acquired (Step S131). In a case where the entire surface (that is, a range including all of the light emitting elements 53) is set as the light emitting range as in Embodiment 1, all of the light emitting elements 53 are counting targets.

As described above, according to the biological information acquisition method in this embodiment, in addition to the advantageous effect in Embodiment 1, the light emitting frequency or the light emitting time of the light emitting elements 53 can be more accurately counted. Accordingly, it is possible to reduce a decrease in the luminance (light emitting power) which is caused by element deterioration. It is possible to secure the light quantity required for obtaining the light receiving result once, and it is possible to sufficiently accurately acquire the biological information relating to the blood vessel.

The invention is not limited to the above-described embodiments, and various modifications or improvements can be added to the above-described embodiments. The modification examples will be described below.

Modification Example 1

In order to make the luminance (light emitting power) in the measurement-purpose light emitting unit Ld substantially the same as the luminance (light emitting power) in the reference-purpose light emitting unit Lr, the product of the light emitting frequency and the light emitting time of the light emitting elements 53 in order to obtain the light receiving result once in the measurement-purpose light emitting unit Ld may be made substantially the same as the product of the light emitting frequency and the light emitting time of the light emitting elements 53 in order to obtain the light receiving result once in the reference-purpose light emitting unit Lr. More specifically, the product of the light emitting frequency and the light emitting time of the light emitting elements 53 in order to obtain the light receiving result once in the measurement-purpose light emitting unit Ld may be set in a range of 80% to 120% of the product of the light emitting frequency and the light emitting time of the light emitting elements 53 in order to obtain the light receiving result once in the reference-purpose light emitting unit Lr.

Modification Example 2

In the above-described embodiments, after the step (Step S180) of acquiring the first light receiving result Q1, the step (Step S210) of acquiring the second light receiving result Q2 is performed. However, the invention is not limited thereto. A method may be used in which the first light receiving result Q1 is acquired after the second light receiving result Q2 is acquired.

Modification Example 3

In the above-described embodiments, after the light emitting unit L and the light receiving unit S are selected (for example, Step S160), the light emitting unit L emits the light (for example, Step S170). However, the invention is not limited thereto. After the light emitting unit L emits the light, the light receiving unit S may be selected.

Modification Example 4

In the above-described embodiments, after the light emitting unit L is selected, the light receiving unit S which is separated from the light emitting unit L by the predetermined distance W is selected. However, the invention is not limited thereto. After the light receiving unit S is selected, the light emitting unit L which is separated from the light receiving unit S by the predetermined distance W may be selected.

Modification Example 5

In the above-described embodiments, the blood glucose level is acquired as the biological information. However, the invention is not limited thereto. For example, as the biological information, oxygen saturation in the blood may be acquired.

Modification Example 6

In the above-described embodiments, the light emitting unit L at the position which is not located above the blood vessel 4 is selected as the reference-purpose light emitting unit Lr, and the reference-purpose light receiving unit Sr which is separated from the reference-purpose light emitting unit Lr by the predetermined distance W and which is not located above the blood vessel 4 is selected. However, the invention is not limited thereto. That is, in addition to the above-described condition, a condition may be added which does not include a position located above the blood vessel between the reference-purpose light emitting unit Lr and the reference-purpose light receiving unit Sr. In this manner, the second light receiving result Q2 obtained by the reference-purpose light receiving unit Sr has a smaller proportion of the emitted light passing through the blood vessel. Accordingly, the second light receiving result Q2 has less information relating to the blood vessel or the blood inside the blood vessel. As a result, the biological information can be accurately acquired.

The elements other than the elements described in the independent claims among the configuration elements in the above-described embodiments and modification examples are additional elements, and may be appropriately omitted.

The entire disclosure of Japanese Patent Application No. 2016-163348, filed Aug. 24, 2016 is expressly incorporated by reference herein.

What is claimed is:

1. A biological information acquisition device comprising:
   a light source having a plurality of LEDs, each of the plurality of LEDs being configured to emit light to a living body;
   an image sensor configured to receive the light transmitted through the living body;
   a memory configured to store a program and a predetermined number of light emissions of each of the plurality of LEDS; and
   a processor configured to execute the program so as to:
      repeatedly activate the light source to cause the plurality of LEDs to emit the light to the living body so that the image sensor receives the light transmitted through the living body;
      after the repeated activating of the light source, cause the image sensor to output a signal corresponding to the received lights passing through the living body;
      acquire information of the living body in response to the signal from the image sensor;
      count a number of light emissions of the plurality of LEDs; and
      determine whether the counted number of light emissions is more than the predetermined number of light emissions,
   wherein, when the processor determines that the counted number of light emissions is more than the predetermined number of light emissions, the processor increases a number of the repeated activations of the light source in a subsequent measurement to acquire the information of the living body.

2. The biological information acquisition device according to claim 1,
   wherein the image sensor is configured with a first image sensor and a second image sensor,
   the first image sensor is configured to receive the light transmitted through a blood vessel of the living body; and
   the second image sensor is configured to receive the light transmitted through an area of the living body that is spaced apart from the blood vessel.

3. The biological information acquisition device according to claim 2,
   wherein the information of the living body is glucose concentration or oxygen saturation in blood in the blood vessel.

4. A biological information acquisition method of acquiring biological information by using a biological information acquisition device, the biological information acquisition device including:
   a light source having a plurality of LEDs, each of the plurality of LEDs being configured to emit light to a living body,
   an image sensor configured to receive the light transmitted through the living body,
   a memory configured to store a program and a predetermined number of light emissions of each of the plurality of LEDs, and
   a processor configured to execute the program,
   the method comprising executing in the processor the steps of:
      repeatedly activating the light source to cause the plurality of LEDs to emit the light to the living body so that the image sensor receives the light transmitted through the living body;
      after the repeated activating of the light source, causing the image sensor to output a signal corresponding to the received lights passing through the living body;
      acquiring information of the living body in response to the signal from the image sensor;
      counting a number of light emissions of the plurality of LEDs; and
      determining whether the counted number of light emissions is more than the predetermined number of light emissions,
   wherein, when the processor determines that the counted number of light emissions is more than the predetermined number of light emissions, the processor increases a number of the repeated activations of the light source in a subsequent measurement to acquire the information of the living body.

* * * * *